(12) United States Patent
Jacoby et al.

(10) Patent No.: US 11,911,567 B2
(45) Date of Patent: Feb. 27, 2024

(54) FLOW SWITCHING VALVE AND METHOD OF USE IN VENTILATING MULTIPLE PATIENTS WITH A SINGLE VENTILATOR

(71) Applicant: Robert Jacoby, Castaic, CA (US)

(72) Inventors: Robert Jacoby, Castaic, CA (US); Kristin Jacoby, Granada Hills, CA (US); Allen Lu, City of Industry, CA (US)

(73) Assignee: Robert Jacoby, Castaic, CA (US)

( * ) Notice: Subject to any disclaimer, the term of this patent is extended or adjusted under 35 U.S.C. 154(b) by 415 days.

(21) Appl. No.: 17/215,662

(22) Filed: Mar. 29, 2021

(65) Prior Publication Data

US 2021/0299395 A1 Sep. 30, 2021

Related U.S. Application Data

(60) Provisional application No. 63/007,767, filed on Apr. 9, 2020, provisional application No. 63/001,217, filed on Mar. 27, 2020.

(51) Int. Cl.
*A61M 16/00* (2006.01)
*A61M 16/20* (2006.01)
*F24F 11/00* (2018.01)
*A61M 16/06* (2006.01)
*A61M 16/04* (2006.01)

(52) U.S. Cl.
CPC ........ *A61M 16/20* (2013.01); *A61M 16/0057* (2013.01); *A61M 16/04* (2013.01); *A61M 16/06* (2013.01); *A61M 16/0666* (2013.01); *A61M 16/208* (2013.01); *F24F 11/0001* (2013.01)

(58) Field of Classification Search
CPC .. A61M 16/20; A61M 16/0057; A61M 16/04; A61M 16/06; A61M 16/0666; A61M 16/208; F24F 11/0001
See application file for complete search history.

(56) References Cited

U.S. PATENT DOCUMENTS

| | | | | |
|---|---|---|---|---|
| 5,752,507 A | * | 5/1998 | Moalem | A61M 16/0404 128/204.21 |
| 2002/0072322 A1 | * | 6/2002 | Sharp | F24F 11/63 454/229 |
| 2005/0095978 A1 | * | 5/2005 | Blunn | F24F 11/0001 454/229 |

* cited by examiner

*Primary Examiner* — Steven O Douglas
(74) *Attorney, Agent, or Firm* — Maschoff Brennan

(57) ABSTRACT

An airflow switching valve allowing a single ventilator to sequentially ventilate multiple patients, each patient being ventilated through a respiratory cycle. The airflow switching valve includes an outer housing, an inner housing, and a spring. Each of the outer and inner housings have a plurality of apertures that, when aligned in different positions, direct airflow to different patients. The inner housing rotates within the outer housing into different positions. The rotational movement is guided by a track of the outer housing. Extensions on the inner housing engage the track of the outer housing and translate along the track, thereby directing the movement of the inner housing between varying positions. Movement of the inner housing is initiated by either a spring force caused by the spring of the airflow switching valve or by air pressure caused by an inspiratory breath flowing into the airflow switching valve from the ventilator.

27 Claims, 19 Drawing Sheets

FLOW SWITCHING VALVE AND METHOD OF USE IN VENTILATING MULTIPLE PATIENTS WITH A SINGLE VENTILATOR

FIELD OF THE INVENTION

The present invention, in general, relates to ventilators and, more particularly, to a flow switching valve for use with ventilators to ventilate two or more patients with a single mechanical ventilator.

BACKGROUND OF THE INVENTION

Background description includes information that may be useful in understanding the present invention. It is not an admission that any of the information provided herein is prior art or relevant to the presently claimed invention, or that any publication specifically or implicitly referenced is prior art.

Ventilators are used to ventilate a patient's lungs with breathable air/breathe, thereby assisting patients when their ability to breathe on their own is somehow impaired. Ventilators are primarily used in intensive-care medicine, home care, emergency medicine as standalone units and in anesthesiology.

Respiratory distress may occur due to the onset of an epidemic or pandemic disease state. Respiratory distress, among other symptoms, includes an impaired ability of the patient to maintain efficient oxygenation. In the current Covid-19 pandemic, a significant percentage of patients developed a severe clinical state that led to acute respiratory distress syndrome resulting in a huge demand of the lifesaving ventilators. Shortage of the ventilators was highlighted globally during the ongoing pandemic. In many countries, the doctors had to decide among patients who would receive mechanical ventilation due to the shortage.

Alternatives are sought globally to increase the ventilation capacity for patients as procuring mechanical ventilators in such large quantity may not be feasible due to several factors including but not limited to high cost.

Many innovators have attempted ventilating two or more patients with one mechanical ventilator using splitting connectors. These connectors split the flow of gases to multiple patients at the same time. These attempts have ultimately failed because the lungs of patients are not identical, and change in volume, pressure, and compliance of the lungs of patients may change during treatment. Thereby, splitting the breath can be so dangerous for the patients, that there is a risk of losing two patients instead of one.

Thus there is a requirement of a device, system, and method thereof that enables ventilating two or more patients through a single ventilator.

SUMMARY OF THE INVENTION

To overcome the problems of the prior art, the present invention provides an airflow switching valve to ventilate more than one patient at a time. The airflow switching valve of the present invention can be used with the existing mechanical ventilators without any requirement of modifying the ventilators. The airflow switching valve allows full ventilator control to each patient individually i.e., breath from the ventilator is circulated to each of the patient with the varying input pressure and or other parameters. Also, the airflow switching valve do not require power supply to operate.

In order to ventilate more than one patient at a time, the airflow switching valve is placed between a mechanical ventilator inspiratory port and a ventilatory circuit to alternate airflow between two patients after each inspiratory breath generated by the mechanical ventilator. The airflow switching valve allows a single ventilator to sequentially ventilate the patients, such that a first patient is ventilated through a respiratory cycle before moving on to a second patient; the second patient is in turn ventilated through a respiratory cycle. In this way, the ventilator can function normally for each patient on every other breath, without abandoning principles of mechanical ventilatory management.

The airflow switching valve comprises an outer housing having a plurality of first openings and an inner housing having a plurality of second openings. A pressurized airflow (i.e., an inspiratory breath containing the breathable gas) from the ventilator aligns a second opening from the plurality of second opening with a first opening from the plurality of first openings to sequentially ventilate the two or more patients. The plurality of the openings in the outer housing and inner housing when aligned in different positions, direct airflow to different patients. The inner housing (e.g., including a body of the inner housing) is rotatable and translatable within the outer housing in order to move (e.g., rotate and translate) into different positions. The movement of the inner housing within the outer housing (e.g., rotational movement and/or translational movement) is guided by a track of the outer housing. Extensions (e.g., pins, pegs, and the like) on the inner housing engage a guide (e.g., a track) of the outer housing and translate along the track, thereby directing the movement of the inner housing between varying positions within the outer housing. Movement of the inner housing is initiated by either a spring force caused by the spring of the airflow switching valve or by air pressure caused by an inspiratory breath flowing into the airflow switching valve from the mechanical ventilator.

In one embodiment, an airflow switching valve includes an outer housing having a first end and a second end. The outer housing includes a first wall extending between the first end and the second end of the outer housing, the first wall partially defining a first volume. The outer housing also includes a second wall connected to the first wall, the second wall being at or adjacent to the first end of the outer housing and forming a closed end of the outer housing. The outer housing also includes a plurality of first openings through the first wall and a track in or on the first wall. The airflow switching valve also includes an inner housing disposed within the first volume. The inner housing includes a body, a plurality of second openings through a surface of the body, and a plurality of extensions extending away from the surface of the body. The plurality of extensions are at least partially disposed and translatable within the track. The airflow switching valve also includes a spring disposed within the first volume, the spring extending between the closed end of the outer housing and the inner housing.

In one embodiment, the inner housing is rotatable relative to the outer housing about an axis of rotation, between a plurality of positions, where a shape of the track defines the plurality of positions.

In one embodiment, the plurality of positions includes a first airflow position, in which one first opening of the plurality of first openings through the first wall of the outer housing is aligned with one second opening of the plurality of second openings through the surface of the body of the inner housing. The plurality of positions also includes a second airflow position, in which another first opening of the plurality of first openings through the first wall of the outer housing is aligned with another second opening of the plurality of second openings through the surface of the body of the inner housing.

In one embodiment, the airflow switching valve is operable to provide airflow from a single ventilator to a first patient when the inner housing is in the first airflow position. The airflow switching valve is also operable to provide airflow from the single ventilator to a second patient when the inner housing is in the second airflow position.

In one embodiment, the plurality of positions includes an intermediate position. No first openings of the plurality of first openings through the first wall of the outer housing overlap with any second openings of the plurality of second openings through the surface of the body of the inner housing when the inner housing is in the intermediate position relative to the outer housing.

In one embodiment, the plurality of first openings through the first wall of the outer housing are aligned linearly along the first wall of the outer housing.

In one embodiment, the plurality of second openings through the surface of the body of the inner housing includes two second openings, where one of the two second openings is opposite the other of the two second openings.

In one embodiment, the first wall of the outer housing is a first annular wall, and the track is in or on an inner surface of the first annular wall. In this embodiment, the body of the inner housing includes a second annular wall. The plurality of second openings extend through the second annular wall, and the plurality of extensions extend away from an outer surface of the second annular wall.

In one embodiment, the plurality of extensions are pegs.

In one embodiment, the track is wave shaped, and the track includes a first side and a second side opposite the first side. Each side of the first side and the second side includes a plurality of alternating crest-shaped portions and trough shaped portions, where the plurality of alternating crest-shaped portions and trough-shaped portions of the first side of the track are substantially aligned with the plurality of alternating crest-shaped portions and trough-shaped portions of the second side of the track.

In one embodiment, the plurality of trough-shaped portions of the first side of the track are offset from the plurality of trough-shaped portions of the second side of the track in a first direction. The plurality of crest-shaped portions of the first side of the track are offset from the plurality of crest-shaped portions of the second side of the track in a second direction opposite the first direction.

In one embodiment, the offset in the first direction and the offset in the second direction are configured to allow the inner housing to rotate in a first rotational direction and prevent the inner housing from rotating in a second rotational direction opposite the first rotational direction.

In one embodiment, the inner housing includes a first section disposed proximate the closed end of the outer housing, the first section including the plurality of extensions and configured to receive the spring. The inner housing also includes a second section including the plurality of second openings, where a first space inside the first section is physically separate from a second space inside the second section.

In one embodiment, the outer housing, the inner housing, the first section of the inner housing, and the second section of the inner housing are cylindrically shaped.

In one embodiment, the first end of the outer housing, the second end of the outer housing, the plurality of first openings through the first wall, the plurality of second openings through the surface of the body, and the plurality of extensions of the inner housing are circular shaped.

In one embodiment, the outer housing and the inner housing are made of a thermoplastic polymer.

In one embodiment, a system operable to provide artificial respiration to at least two patients using a single ventilator is provided. The system includes a mechanical ventilator. The system also includes an airflow switching valve. The airflow switching valve includes an outer housing. The outer housing includes a plurality of first apertures and a track. The airflow switching valve also includes an inner housing disposed inside the outer housing. The inner housing includes a plurality of second apertures and a plurality of extensions. The plurality of extensions are configured to translate within the track of the outer housing to rotate the inner housing between a plurality of positions. The system also includes at least two patient interfaces. The system also includes at least two on-way valves. The system also includes an air circuit connecting the mechanical ventilator, the airflow switching valve, and the at least two one-way valves to the at least two patient interfaces, such that the system is operable to provide a breathable gas to the at least two patients.

In one embodiment, the mechanical ventilator is operable to generate an inspiratory breath containing the breathable gas to the air circuit. The air circuit is operable to transfer the inspiratory breath from the mechanical ventilator to the airflow switching valve, and transfer the inspiratory breath from the airflow switching valve to the at least two patient interfaces in an alternating manner depending on a position of the plurality of positions of the inner housing inside the outer housing of the airflow switching valve, such that only a single patient interface of the at least two patient interfaces receives the inspiratory breath.

In one embodiment, the air circuit is operable to transfer an expiratory breath from a patient interface of the at least two patient interfaces to the at least two one-way valves and transfer the expiratory breath from the at least two oneway valves to the mechanical ventilator.

In one embodiment, the airflow switching valve is operable to provide the breathable gas from the mechanical ventilator to a first patient of the at least two patients when the inner housing is in a first position of the plurality of positions, and the airflow switching valve is operable to provide the breathable gas to a second patient of the at least two patients when the inner housing is in a second position of the plurality of positions.

In one embodiment, one first aperture of the plurality of first apertures of the outer housing is aligned with one second aperture of the plurality of second apertures of the inner housing in the first position. Another first aperture of the plurality of first apertures of the outer housing is aligned with another second aperture of the plurality of second apertures of the inner housing in the second position.

In one embodiment, a method for providing inspiratory breaths to multiple patients sharing a single ventilator on an artificial breathing system is provided. The artificial breathing system includes an airflow switching valve. The airflow switching valve includes an outer housing and an inner housing. The outer housing includes a plurality of first apertures and a track. The inner housing includes a plurality of second apertures and a plurality of extensions. The plurality of extensions are configured to translate within the track of the outer housing to rotate the inner housing between a plurality of positions. The method includes generating, by the single ventilator, a first inspiratory breath for a first patient of the multiple patients. The method also includes receiving, by the airflow switching valve, the first inspiratory breath. The method also includes providing, by the airflow switching valve, the first inspiratory breath to the first patient of the multiple patients when the inner housing is in a first position of the plurality of positions.

In one embodiment, the method also includes generating, by the single ventilator, a second inspiratory breath for a second patient of the multiple patients. The method also includes receiving, by the airflow switching valve, the second inspiratory breath. The method also includes providing, by the airflow switching valve, the second inspiratory breath to the second patient of the multiple patients when the inner housing is in a second position of the plurality of positions.

In one embodiment, the method includes repeating the generating, receiving, and providing for another inspiratory breath for the first patient after the generating, receiving, and providing the second inspiratory breath.

In one embodiment, the first position is when one first aperture of the plurality of first apertures of the outer housing is aligned with one second aperture of the plurality of second apertures of the inner housing.

In one embodiment, the second position is when another first aperture of the plurality of first apertures of the outer housing is aligned with another second aperture of the plurality of second apertures of the inner housing.

In one embodiment, the airflow switching valve further includes a spring positioned between the outer housing and the inner housing. The spring is compressed in a breath state and extended in a non-breath state, the breath state being when the airflow switching valve receives the first inspiratory breath or the second inspiratory breath, the non-breath state being when the airflow switching valve is not receiving the first inspiratory breath or the second inspiratory breath. Receiving the first inspiratory breath causes the inner housing to compress the spring and simultaneously rotate into the first position by way of the plurality of extensions translating within the track of the outer housing. After providing the first inspiratory breath to the first patient, the spring is configured to extend and cause the inner housing to rotate into an intermediate position by way of the plurality of extensions translating within the track of the outer housing. The intermediate position is between the first position and the second position. Receiving the second inspiratory breath causes the inner housing to compress the spring and simultaneously rotate into the second position by way of the plurality of extensions translating within the track of the outer housing. After providing the second inspiratory breath to the second patient, the spring is configured to extend and cause the inner housing to rotate into another intermediate position by way of the plurality of extensions translating within the track of the outer housing. The other intermediate position is between the second position and the first position.

Any one or more of the aspects described above may be used alone or in combination. These and other aspects, features and advantages will become apparent from the following detailed description of embodiments, which is to be read in connection with the accompanying drawings. The present disclosure is defined by the following claims, and nothing in this section should be taken as a limitation on those claims. Further aspects and advantages of the disclosure are discussed below in conjunction with the embodiments and may be later claimed independently or in combination.

BRIEF DESCRIPTION OF THE DRAWING

The components and the figures are not necessarily to scale, emphasis instead being placed upon illustrating the principles of the disclosure. Moreover, in the figures, like reference numerals designate corresponding parts throughout the different views.

DETAILED DESCRIPTION OF THE INVENTION

Figure 1:
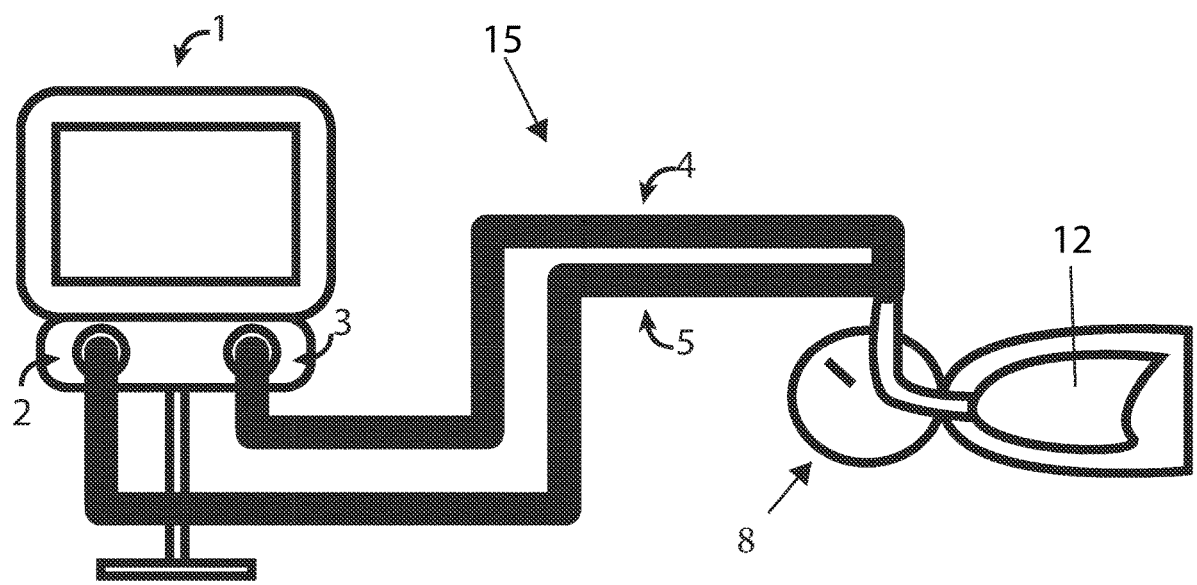
FIG. 1 shows a schematic diagram of a system of prior art for ventilating one patient using a mechanical ventilator.

The attempts to ventilate two or more patients with one mechanical ventilator of the prior art have ultimately failed because the lungs of patients are not identical, and change in volume, pressure, and compliance of the lungs of patients may change during treatment. The present embodiments address this with the use of an airflow switching valve placed between the mechanical ventilator and two or more patients to allow for the safe ventilation of the two or more patients (e.g., a shared ventilator mode).

The airflow switching valve functions by allowing the mechanical ventilator to provide gases through either an inspiratory cycle or through an entire respiratory cycle to a single patient before switching to a second patient, allowing the mechanical ventilator to ventilate each patient individually and sequentially in an alternating manner. In other words, the ventilator gives patient number one a single breath, allows patient number one to exhale, then the airflow switching valve switches the airflow over and lets the ventilator give patient number two a full breath. Virtually all currently used mechanical ventilators can be retrofitted with the disclosed airflow switching valve.

It is noted that while using the shared ventilator mode, mechanical ventilator settings may need to remain the same across the two or more patients. However, using pressure control settings and adjusted respiratory rate will allow most pairs of patients to be ventilated with a small amount of over-ventilation. The ventilator still remains compliant and responsive to each individual patient breath It is also noted that the shared ventilator mode may work best with sedated patients to prevent patients from taking spontaneous breaths.

In one example, pressure control settings with a rate control of two times a normally desired rate adjusts well in the shared ventilator mode. Alternatively, a decrease in an inspiratory to expiratory ratio may produce a same or similar result. Volume control settings with peak pressures adjusted to a less compliant lung may also produce similar results. Peak end expiratory pressures may not influence the shared ventilator mode. Both a coupled expiratory/inspiratory valve setup and an independent flow switching valve with one-way valves on an expiratory hose may not impede peak end expiratory pressure settings Patients being weaned off a ventilator may not be appropriate for the shared ventilator mode.

For the remainder of this document, two patients, two lungs, two outflows, and various other objects of reference implies two or more patients, two or more lungs, two or more outflows, and various other objects of reference. Similarly, reference to the second object of reference implies the reference to multiple objects in turn.

The drawings are not necessarily to scale. Thus, proportions of the disclosed airflow switching valve and the relative positions of the various features and elements of the airflow switching valve and shared ventilatory mode system may vary from the examples shown and described herein. The use of terms herein, such as "top," "bottom," "left," "right," "forward," "rearward," "front," "rear," "side," "upper," "lower," "upward," "downward," "inner," "outer," "first," "second," and the like are meant only to differentiate among elements having similar names or different positions. Such terms are used herein merely for reference and are not intended to limit the scope of such elements to a particular order, side, height, orientation, position, or the like, of any components of the airflow switching valve except where expressly and specifically stated.

As employed herein, the statement that two or more parts are "connected" or "coupled" together shall mean that the parts are joined together either directly or joined together through one or more intermediate parts. Further, as employed herein, the statement that two or more parts are "attached" together shall mean that the parts are joined together directly.

It is to be understood that elements and features of the various representative embodiments described below may be combined in different ways to produce new embodiments that likewise fall within the scope of the present teachings.

FIG. 1 shows a schematic diagram of a system for ventilating one patient 8 using a mechanical ventilator 1. Conventionally, the lung(s) 12 of a single patient 8 is ventilated using a single ventilator 1. The ventilator 1 typically includes an inspiratory port 3 and an expiratory port 2. An inspiratory hose 4 is connected to the inspiratory port 3 and a patient interface 10, and an expiratory hose 5 is connected to the patient interface 10 and the expiratory port 2. The combination of hoses 4, 5, ventilator 1, and patient interface 10 make up a respiratory circuit 15 or breathing circuit 15. The patient interface 10 may be a mask, such as a nasal mask, oral mask, total face mask that covers the face, or endotracheal tube or nasal cannula, that couples the respiratory circuit 15 to the airway and lung(s) 12 of the patient 8. Other patient interfaces are possible.

Figure 2:
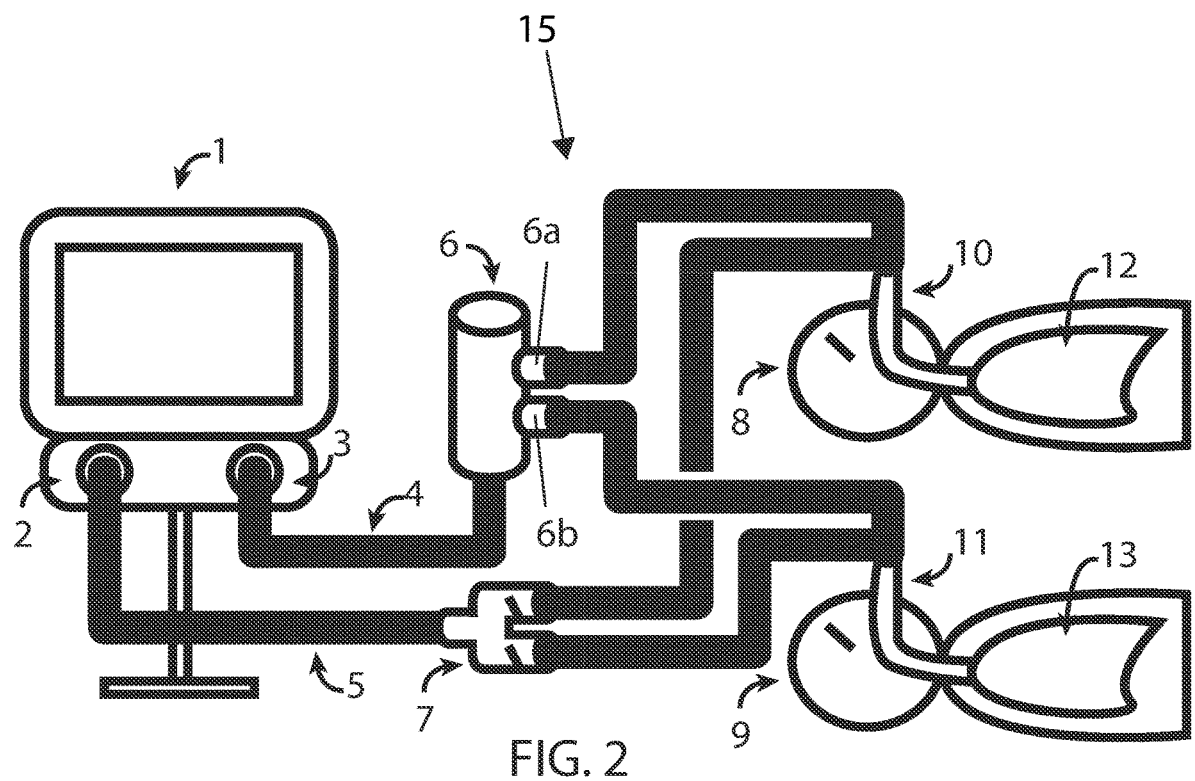
FIG. 2 shows a schematic diagram of one embodiment of a system for ventilating two patients using a mechanical ventilator and an airflow switching valve.

FIG. 2 shows a schematic diagram of one embodiment of a system for ventilating two patients 8, 9 using a mechanical ventilator 1 and an airflow switching valve 6. In one embodiment, the inspiratory port 3 of the mechanical ventilator 1 is attached to the airflow switching valve 6 via an inspiratory hose 4. The airflow switching valve 6 includes two outflow ports 6a, 6b. The first outflow port 6a is connected to the first patient interface 10 of the first patient 8 via a tube or hose. The second outflow port 6b of the airflow switching valve 6 is connected to a second patient interface 11 of the second patient 9 via another tube or hose. Tubes or hoses are also connected between the respective first and second patient interfaces 10, 11 and respective one-way valves 7. In the embodiment shown in FIG. 2, the one-way valves 7 are housed by a single common housing.

The one-way valves 7 are connected to the expiratory port 2 via a single hose (e.g., the expiratory hose 5). The one-way valves 7 attached to the expiratory hose 5 of the mechanical ventilator prevent back flow and flow between the first and second patients 8, 9. The inspiratory port 3 of the mechanical ventilator 1 provides a positive pressure flow of gases, such as oxygen, from the mechanical ventilator 1 to the lungs 12, 13 of the patients 8, 9, respectively, through a variety of controls that include pressure, volume, peak pressures, and end expiratory pressures.

In this embodiment, when the mechanical ventilator 1 generates and sends an inspiratory breath, the airflow switching valve 6 opens and directs the airflow (i.e., inspiratory breath) out of the first outflow port 6a to the first patient 8. A triggering mechanism to direct flow to the first patient 8 may consist of pressure and flow resistance generated by the mechanical ventilator 1. At the end of the inspiratory breath delivered by the mechanical ventilator 1 to the first patient 8 (i.e., when the mechanical ventilator 1 stops delivering the inspiratory breath), the airflow switching valve 6 closes or stops the flow and resets for the next inspiratory breath. As will be discussed in more detail below, when the airflow switching valve 6 "resets," the internal components of the airflow switching valve 6 move into a position that prohibits airflow from exiting out of either the first or second outflow ports 6a, 6b. At the next inspiratory breath, the airflow switching valve 6 directs flow out of the second outflow port 6b to the second patient 9.

In one embodiment, the mechanical ventilator 1 is able to detect, monitor, and control the inspiratory breath of the first patient 8 through traditional controls of ventilatory volume, pressure, peek pressure, speed, end expiratory pressure and rate throughout the respiratory cycle. At the next inspiratory breath, the mechanical ventilator 1 is able to control the inspiratory breath of the second patient 9 separately without interference from the first patient 8.

Figure 3:
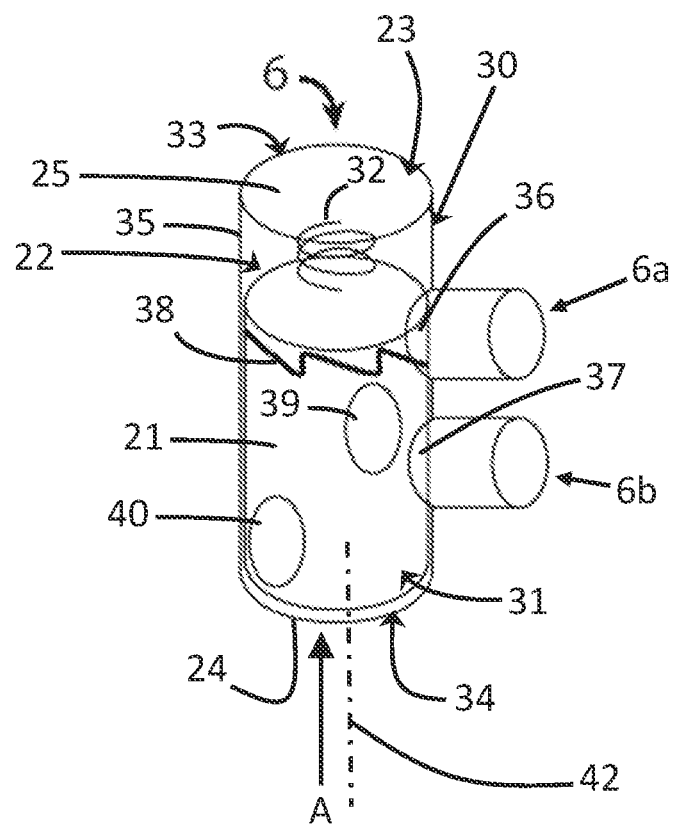
FIG. 3 illustrates one embodiment of the airflow switching valve of FIG. 2.

FIG. 3 illustrates one embodiment of the airflow switching valve 6 of FIG. 2. The airflow switching valve 6 includes an outer housing 30 at least partially defining an outer chamber, and an inner housing 31 at least partially defining an inner chamber. The inner housing 31 is radially inner (e.g., inside) the outer housing 30. In other words, the inner housing 31 is radially inner relative to the outer housing 30. The airflow switching valve 6 also includes a spring 32.

The outer housing 30 includes a first end 23, a second end 24, and a first wall 35 that at least partially defines the outer housing 30 and that extends between the first end 23 and the second end 24 of the outer housing 30. The first wall 35 at least partially defines a first volume 22. The outer housing 30 also includes a second wall 25 connected to the first wall 35. The second wall 25 is at or adjacent to the first end 23 of the outer housing 30 and forms a closed end 33 of the outer housing 30. The outer housing 30 also includes a plurality of first openings (e.g., apertures) 36, 37 in (e.g., through) the first wall 35. In one embodiment, the plurality of first openings include two first openings 36, 37. More or fewer first openings may be provided. The outer housing 30 also includes a track 38 in or on the first wall 35. The track is disposed within or extends away from an inner surface of the first wall 35. In one embodiment, the second end 24 is an open end 34 and is configured to be coupled to tubing, such as the inspiratory hose 4 of FIG. 2. In this example, the open end 34 of the outer housing 30 is configured to receive air inflow A from the ventilator 1 through the inspiratory hose 4.

The inner housing 31 is disposed within the first volume 22 of the outer housing 30 and includes a body 21. The inner housing 31 also includes a plurality of second openings (e.g., apertures) 39, 40 in (e.g., through) a surface of the body 21 of the inner housing 31. In one embodiment, the plurality of second openings include two second openings 39, 40. More or fewer second openings may be provided. The inner housing 31 also includes a plurality of extensions 41, such as pegs or pins, (see FIGS. 5A and 5B). The plurality of extensions 41, for example, extend away from the surface of the inner housing 31. The plurality of extensions 41 are at least partially disposed and translatable within the track 38 of the first wall 35 of the outer housing 30. The spring 32 is disposed within the first volume 22 and extends between the closed end 33 of the outer housing 30 and the inner housing 31.

The inner housing 31 (e.g., including the body 21) may be rotatable relative to the outer housing 30 about an axis of rotation 42. In this regard, the inner housing 31 may be rotatable within the outer housing 30 between a plurality of positions. In one embodiment, a shape of the track 38 defines the plurality of positions. In one example, the plurality of positions may include a first airflow position, in which one first opening 36 of the plurality of first openings through the first wall 35 of the outer housing 30 is aligned with one second opening 39 of the plurality of second openings through the surface of the body 21 of the inner housing 31. The plurality of positions may also include a second airflow position, in which another first opening 37 of the plurality of first openings through the first wall 35 of the outer housing 30 is aligned with another second opening 40 of the plurality of second openings through the surface of the body 21 of the inner housing 31. The plurality of positions may also include an intermediate position where no first openings of the plurality of first openings 36, 37 through the first wall 35 of the outer housing 30 overlap with any second openings of the plurality of second openings 39, 40 through the surface of the body 21 of the inner housing 31.

In this embodiment, the airflow switching valve 6 is operable to provide airflow from a single ventilator to the first patient 8 when the inner housing 31 is in the first airflow position. Similarly, the airflow switching valve 6 is operable to provide airflow from the single ventilator to the second patient 9 when the inner housing 31 is in the second airflow position.

The airflow switching valve 6 may represent an advancement in the use of valves to allow the inflow A of gases or fluids into a combination of housings (e.g., chambers) 30, 31 and an outflow to a plurality of outflow ports 6a, 6b. In one embodiment, sensors may be used to detect various states within and outside the housings 30, 31. An internal or external trigger may follow. The internal or external trigger may control or change the configuration of the inner housing 31 to change a direction of flow to or from different outflow ports 6a, 6b. Triggers, or triggering events, may be electronic triggers configured to actuate a portion of the airflow switching valve 6 based on sensor information, such as sensed pressure and/or flow information. For example, a ventilator, such as the mechanical ventilator 1, may be configured to automatically control/change the configuration of the airflow switching valve 6 to direct flow from one patient to another. Triggers may also be mechanical-based triggers and may be configured to actuate based on mechanical forces, such as pressure and flow. Sensors used may include pressure sensors, flow rate sensors, oxygen sensors, and any other types of sensors typically associated with respiratory ventilators. These sensors may detect various states within and outside the housings 30, 31, including pressure, gas or fluid flow, resistance, and changes of the states. The detected various states may act as a triggering event and may directly control or change the configuration of the housings 30, 31. Other triggers may also control or change the configuration of the housings 30, 31, as discussed above.

Figure 4:
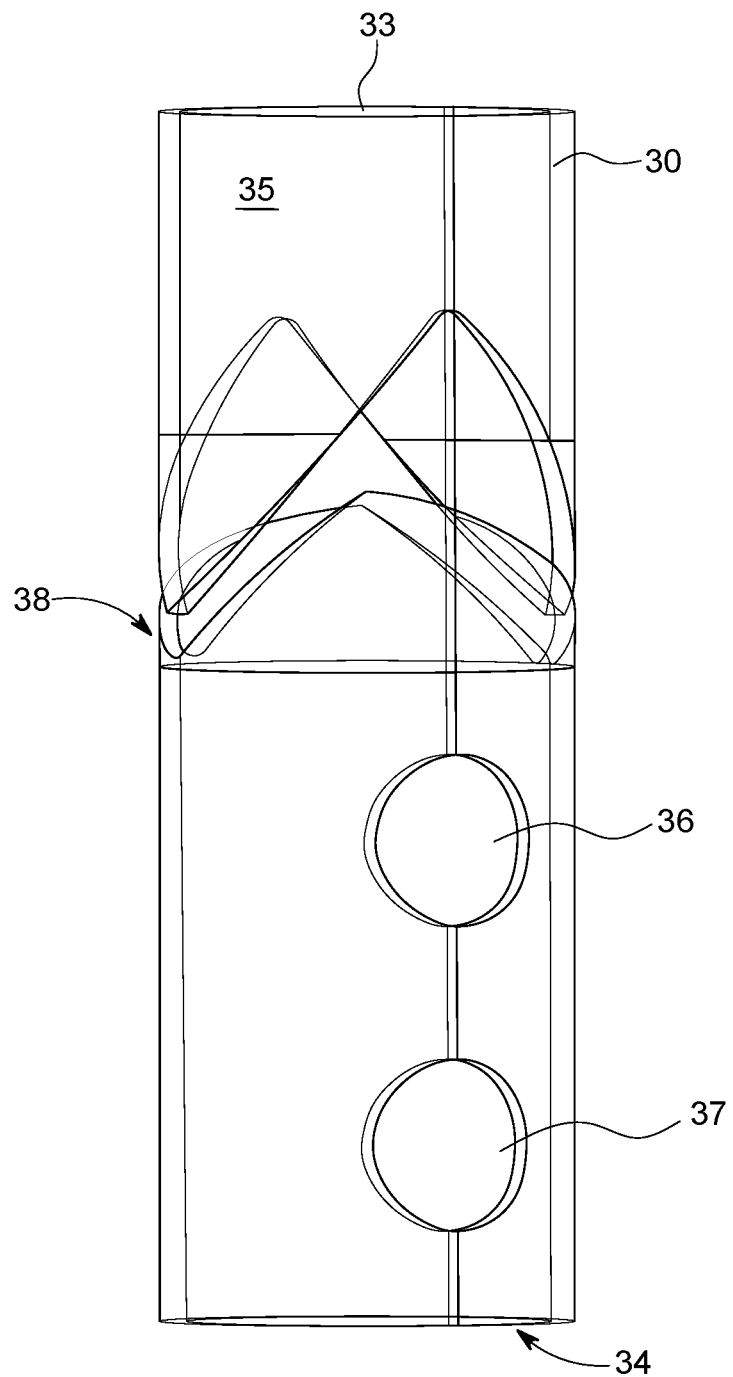
FIG. 4 shows a perspective view of one embodiment of an outer housing of the airflow switching valve of FIG. 3.

FIG. 4 shows a perspective view of one embodiment of an outer housing 30 of the airflow switching valve 6 of FIG. 3. In the example shown in FIG. 4, the plurality of first openings 36, 37 through the first wall 35 of the outer housing 30 are aligned linearly along a longitudinal axis of the first wall 35 of the outer housing 30. Other configurations are possible. For example, one of the first openings 36 may be offset to the left or right of the longitudinal axis (i.e., left or right relative to another of the first openings 37). In another example, as will be discussed below with respect to FIGS. 8B and 8C, one of the first openings 36 and another of the first openings 37 may be arranged on opposite sides of the outer housing 30. As shown in FIG. 4, the track 38 is positioned between one of the first openings 36 and the closed end 33 of the outer housing 30. In one embodiment, the track 38 is wave-shaped, which will be discussed in more detail below with regard to FIGS. 6A and 6B.

In one embodiment, the first wall 35 of the outer housing 30 is a first annular wall and the body 21 of the inner housing 31 is a second annular wall. In this example, the track 38 is in or on an inner surface of the first annular wall, the plurality of second openings 39, 40 extend through the second annular wall, and the plurality of extensions 41 extend away from an outer surface of the second annular wall.

Figure 5A:
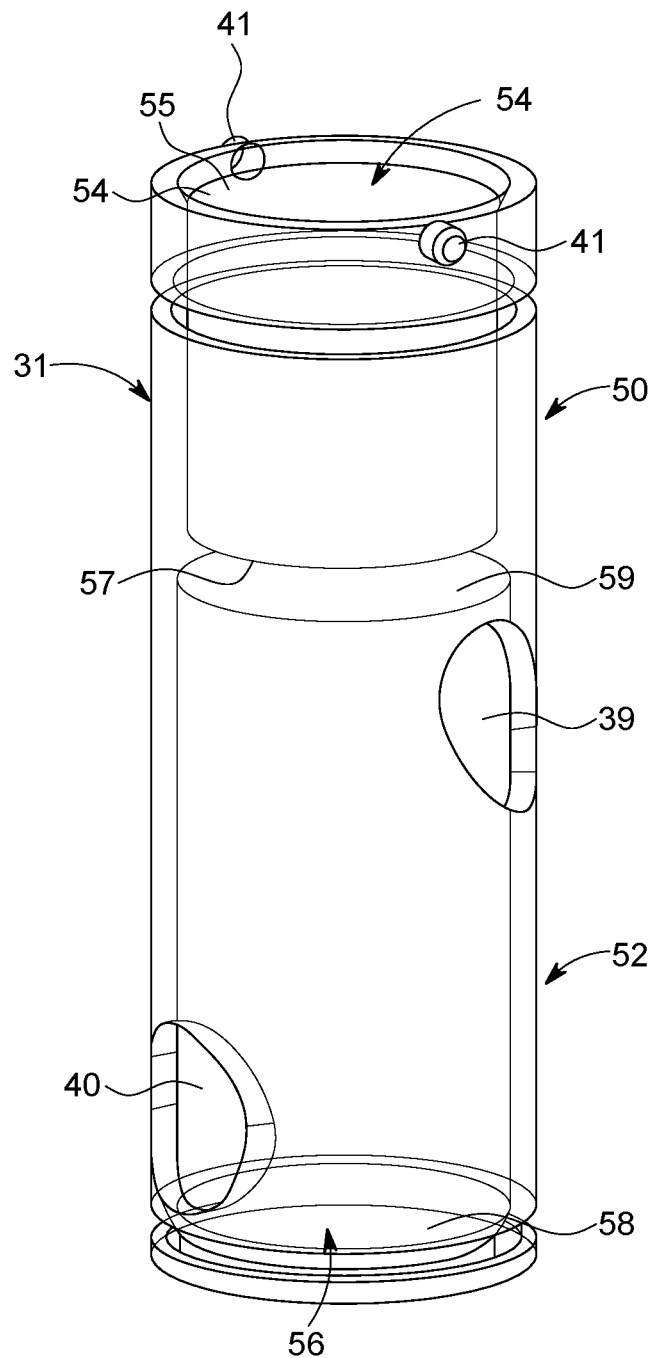
FIGS. 5A-5B show perspective views of one embodiment of an inner housing of the airflow switching valve of FIG. 3.
Figure 5B:
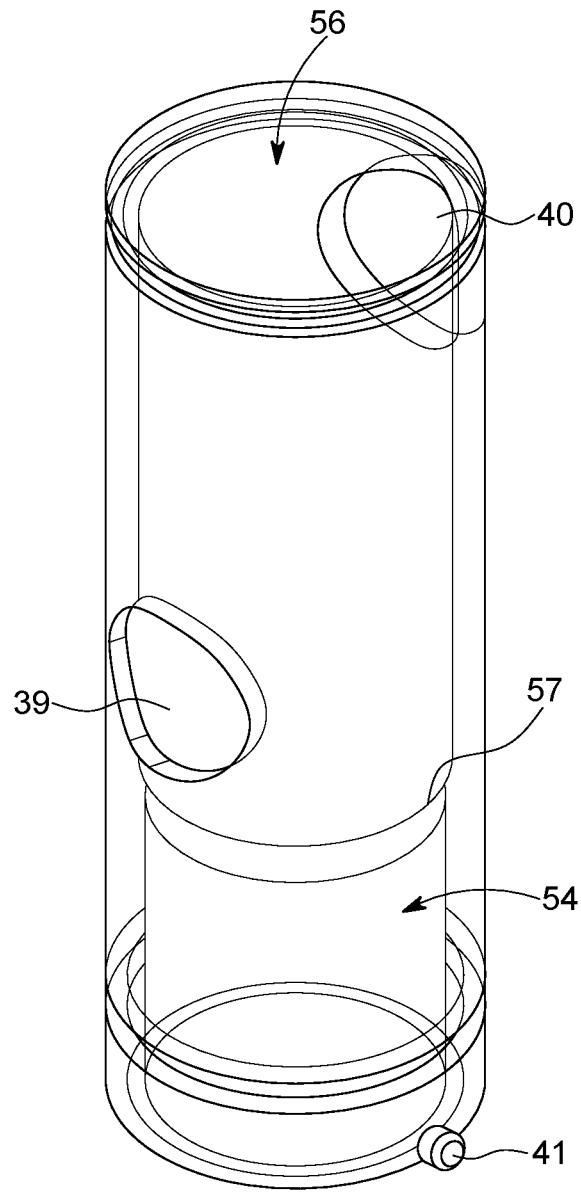

FIGS. 5A-5B show perspective views of one embodiment of an inner housing 31 of the airflow switching valve 6 of FIG. 3. The inner housing 31 of FIG. 5B is the same as the inner housing 31 of FIG. 5A, except the orientation is upside down. As shown in FIGS. 5A-5B, the inner housing 31 includes a first section 50 and a second section 52. The first section 50 is disposed proximate the closed end 33 of the outer housing 30 when the airflow switching valve 6 is assembled. In one example, the first section 50 may be dimensioned to be approximately one third of the entire inner housing 31 and the second section 52 may be dimensioned to be approximately two thirds of the inner housing 31 (e.g., with respect to volume and/or length of the inner housing 31). Other dimensions of the first section 50 and second section 52 may be provided.

The first section 50 of the inner housing 31 includes the plurality of extensions 41. In one embodiment, the plurality of extensions 41 are pegs. Other types of extensions may be provided, such as pins. In one embodiment, the plurality of pegs 41 includes two pegs 41 arranged on opposite sides of the first section 50. A different number of pegs may be used. In one embodiment, the pegs 41 are circular or cylindrically shaped. Other sizes and shapes are possible. For example, the pegs 41 may be shaped as hexagons. In another example, the pegs 41 may be shaped as octagons. A peg 41 may be any type of protuberance or projection, such as a nub, barb, spur, flange, rib, and the like, that rests on, engages, or otherwise cooperates with the track 38 to allow the peg 41 to fit within and translate along the track 38, so that the inner housing 31 may rotate and translate within the outer housing 30. In this way, the track 38 of the outer housing 30 forces the inner housing 31, to rotate and translate in a specific manner to align the plurality of first openings and second openings (e.g., aperture 36 with aperture 39, and aperture 37 with aperture 40). The shape and configuration of the track 38 also prevent the inner housing 31 from rotating backwards (i.e., in a direction towards the previous state or configuration), as will be described below with reference to FIG. 6B.

The first section 50 of the inner housing 31 may also be configured to receive the spring 32. The spring 32 may be a compression spring, such as a straight coil spring, a concave or hourglass spring, a convex or barrel spring, a variable pitch spring, or a volute spring. However, other types of springs may be provided, such as a flat spring, a gas spring, or an air spring. In one example, the first section 50 includes a first portion 54 (e.g., a first space, cavity, volume, interior region, etc.) inside the first section 50. The first space 54 may be cylindrically shaped (e.g., bucket-shaped) and include an open portion 55 adjacent to the pegs 41 and a closed portion 57 opposite the open portion 55. In this embodiment, the spring 32 may at least partially fit within (i.e., received by) the first space 54 of the inner housing 31 and contact the closed portion 57 of the first space 54 and the closed end 33 of the outer housing 30. In this way, the spring 32 is configured to be compressed and extend between the closed end 33 of the outer housing 30 and the closed portion 57 of the first space 54 of the inner housing 31.

The second section 52 of the inner housing 31 includes the plurality of second openings 39, 40. In one embodiment, as shown in FIGS. 5A and 5B, the plurality of second openings 39, 40 are arranged on opposite sides of the inner housing 31 and offset from one another along the direction of the rotational axis 42 (i.e., along the length of the inner housing 31). In this example, one of the second openings 39 is positioned proximate the closed portion 59 of the second space 56 of the second section 52 of the inner housing 31. Another of the second openings 40 is positioned proximate the open portion 58 of the second space 56 of the second section 52 of the inner housing 31. Other configurations are possible. For example, the plurality of second openings 39, 40 may be arranged on the same side of the inner housing 31, albeit offset from one another by a predetermined distance in a direction perpendicular to the direction of the rotational axis 42. In another example, as will be discussed below with respect to FIG. 8A, the plurality of second openings may be arranged at various locations around the body 21 of the inner housing 31 and may include two sets or two pairs of second openings.

As will be discussed below, as pressurized airflow A (e.g., pressurized inspiratory breath generated by the ventilator) enters the second space 56 of the second section 52 of the inner housing 31 of the airflow switching valve 6, the pressure from the airflow A contacting the closed portion 59 of the second section 52 of the inner housing 31 forces the inner housing 31 in a direction towards the spring 32, which causes the spring 32 to be compressed between the closed end 33 of the outer housing 30 and the closed portion 57 of the first space 54 of the inner housing 31. The compression of the spring 32 causes potential energy to be stored in the spring 32 such that, when the airflow A is stopped (i.e., when the ventilator stops generating an inspiratory breath), the spring 32 releases the potential energy and extends between the closed end 33 of the outer housing 30 and the closed portion 57 of the first space 54 of the inner housing 31. This extension of the spring 32 exerts a spring force on the closed portion 57 of the first space 54 of the inner housing 31 in a direction towards the airflow A inlet, which causes the inner housing to move in that same direction (e.g., along the longitudinal axis of the inner housing 31 in a direction towards the airflow A inlet) by way of the track 38 and peg 41 configuration. This movement of the inner housing 31 is what allows the inner housing 31 to move from the first airflow position to an intermediate position, and then to the second airflow position from the intermediate position.

In one embodiment, the outer housing 30, the inner housing 31, the first section 50 of the inner housing 31, and the second section 52 of the inner housing 31 are cylindrically shaped. Likewise, in an embodiment, the closed end 33 of the outer housing 30, the open end 34 of the outer housing 30, the plurality of first openings 36, 37 of the outer housing 30, and the plurality of second openings 39, 40 of the inner housing 31 are circular shaped. Other configurations, sizes and shapes may be provided.

In one embodiment, the outer housing 30, the inner housing 31, and all components thereof, are made of a thermoplastic polymer. For example, acrylonitrile butadiene styrene (ABS) may be used. Other materials may be used. In one embodiment, the outer housing 30, the inner housing 31, and all components thereof, are manufactured by 3D printing, injection molding, or combinations thereof. In one example, all components may first be 3D printed to create models and then injection molds may be formed using the 3D printed models. Other manufacturing methods, now known or later developed, may be used.

In one embodiment, the method of switching the direction of airflow involves the use of the track 38 on the outer housing 30, which rotates and translates the inner housing 31 as a result of pressure and airflow resistance during an inspiratory breath. The inner housing 31 rotates and translates until an aperture 39, 40 in the inner housing 31 lines up with an aperture 36, 37 in the outer housing 30, allowing airflow from the inspiratory hose 4 carrying inflow A to external lines 6a, 6b to specific patients 8, 9. After the inspiratory breath, the inner housing 31 and track 38 reset (e.g., move to an intermediate position) for the next inspiratory breath that would line up another set of apertures (e.g., the next apertures). The track 38 illustrated in FIGS. 6A-6B allows variable pressure and flow, coupled with the spring 32, to reset the inner housing 31 and prevent the inner housing 31 from reversing directions.

The movement of the inner housing 31 within the outer housing 30 and the alignment of second openings 39, 40 with first openings 36, 37, respectively, by utilizing the track 38 is described generally below. The use of terms below, such as "upward," "downward," "clockwise," "counter clockwise," and the like are used merely for reference in conjunction with the corresponding figures and are not intended to limit the scope of such elements to a particular order, side, height, orientation, position, or the like, of any components of the airflow switching valve.

When the mechanical ventilator 1 sends an inspiratory breath, pressure from the inflow (e.g., airflow A) forces the inner housing 31 in an upward direction away from the open end 34 of the outer housing 30 (e.g., upward relative to the open end 34 of the outer housing 30 along the longitudinal axis of the outer housing 30 as shown in FIG. 3) inside the outer housing 30. Due to the shape and configuration of the track 38 and corresponding pegs 41 or protrusions, the inner housing 31 rotates 90 degrees in a first direction (e.g., counterclockwise) so that one of the second openings 39 aligns with one of the first openings 36. Once the apertures 39, 36 are aligned, air flow from the inspiratory hose 4 is allowed through the airflow switching valve 6 and directed to a first patient 8.

When the mechanical ventilator 1 stops delivering the inspiratory breath, the spring 32 exerts a spring force/counter force that forces the inner housing 31 downward away from the closed end 33 of the outer housing 30 (e.g., downward relative to the closed end 33 of the outer housing 30 along the longitudinal axis of the outer housing 30 as shown in FIG. 3). The downward force may cause the inner housing 31 to rotate an additional amount in the same direction (e.g., counter clockwise) as the inner housing 31 previously rotated, thereby breaking the alignment of the apertures 39, 36 and thus stopping the flow out of the airflow switching valve 6. Due to the unique configuration of the pegs 41 or protrusions engaging with the track 38, the inner housing 31 is prevented from rotating in a reverse direction (e.g., clockwise).

Next, at the next inspiratory breath provided by the ventilator 1, the upward force of the inflow A causes the inner housing 31 to rotate another 90 degrees in the same direction as the last 90-degree rotation (e.g., counterclockwise). This rotation is allowed by the track 38 and peg 41 or protrusion configuration. The inner housing 31 moves to a position where another of the second openings 40 aligns with another of the first openings 37. Once these apertures 40, 37 are aligned, air flow from the inspiratory hose 4 is allowed through the airflow switching valve 6 and directed to a second patient 9.

The track 38 is uniquely designed and configured to cooperate with the pegs 41 or protrusions to allow the movement of the inner housing 31 in this fashion so that the inner housing 31 is allowed to rotate, unidirectionally, in a manner that alternates between aligning corresponding different sets of first openings and second openings, sequentially (e.g., first set being the second opening 39 with the first opening 36, and the second set being the second opening 40 with the first opening 37). In this manner, for each 90-degree rotation, different apertures align. In another embodiment, the inner housing 31 may be configured to rotate in 45 degree increments rather than 90-degree increments. In this manner, for each 45-degree rotation, different apertures align. In another embodiment, the inner housing 31 may be configured to rotate both backwards and forwards (e.g., clockwise and counterclockwise) in an alternating and sequential fashion to allow for the alignment of different sets of apertures corresponding to different airflow pathways to different patients.

In another embodiment, the inspiratory hose 4 and expiratory hose 5 of a mechanical ventilator 1 are both attached to another version of the airflow switching valve 6, where control of airflow is coupled through mechanical, pressure, electronic, magnetic, or timing controls.

The movement of the inner housing 31 within the outer housing 30 and the alignment of second openings 39, 40 with first openings 36, 37 by utilizing the track 38 disclosed herein will now be described specifically with reference to FIGS. 6A-6B.

Figure 6A:
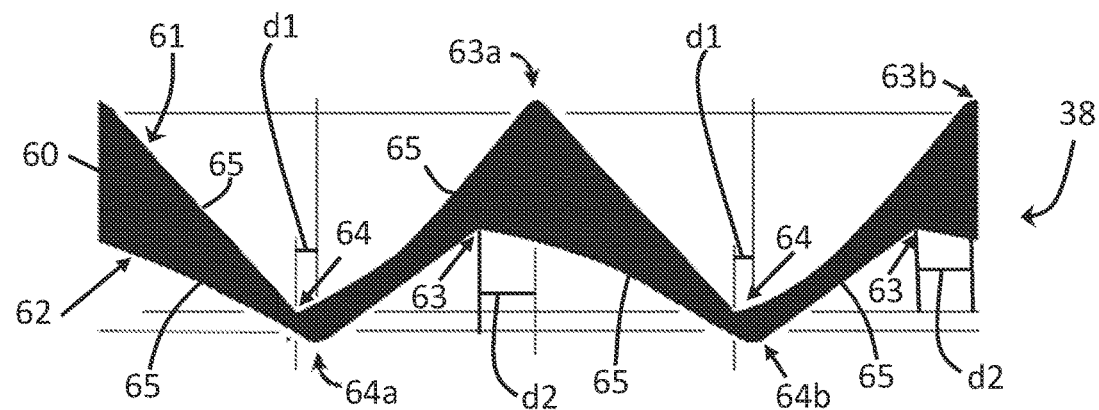
FIGS. 6A-6B show one embodiment of a track of the outer housing of FIG. 4.
Figure 6B:
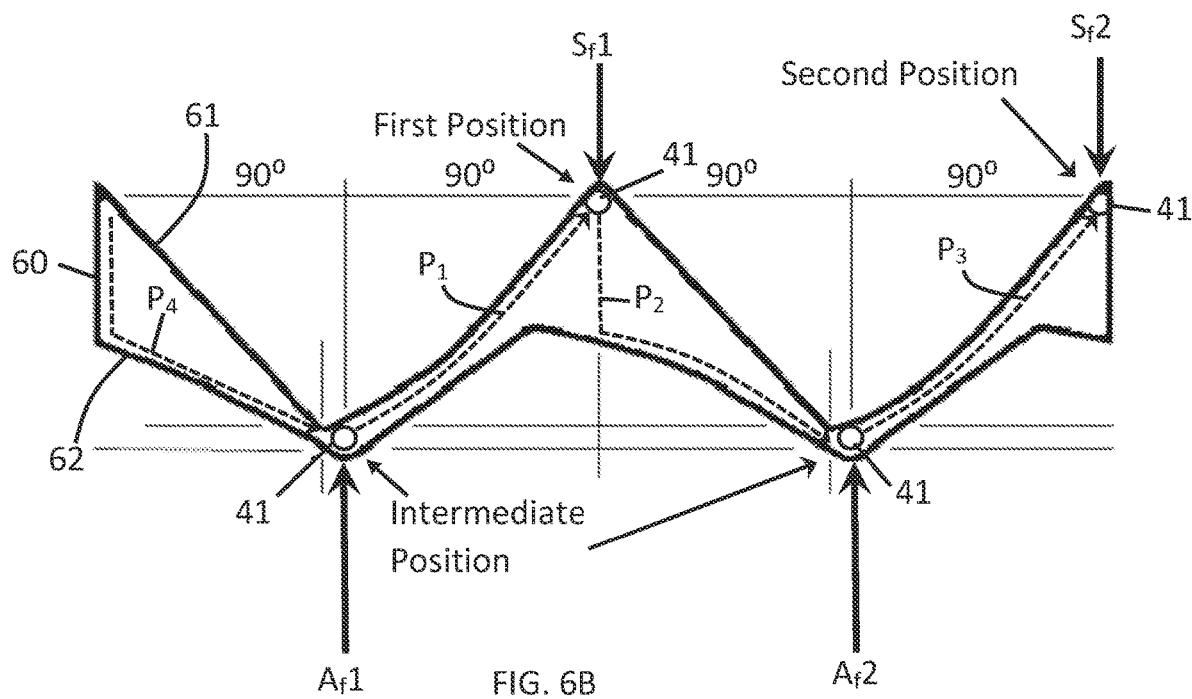

FIGS. 6A-6B show one embodiment of a track 38 of the outer housing 30 of FIG. 4. In the example shown in FIGS. 6A-6B, while the track 38 is disposed on an inner surface of a cylindrically shaped outer housing 30, the track 38 is flattened out in FIGS. 6A-6B for clarity. As mentioned above, in one embodiment, the track 38 may be wave shaped 60. A typical wave formation includes crests (peaks) and troughs (valleys). In this regard, a wave shape or pattern is similar to a zigzag shape or pattern. In one embodiment, the track 38 includes a first side 61 and a second side 62 opposite the first side 61. In this embodiment, each side of the first side 61 and the second side 62 includes a plurality of alternating crest-shaped portions 63 and trough-shaped portions 64. Intermediate portions 65 (e.g., portions between the crest-shaped portions 63 and trough-shaped portions 64) of both the first side 61 and second side 62 of the track 38 may be straight, curved, or combinations and variations thereof. In one example, each of the first side 61 and second side 62 of the track 38 may include a set of two crest-shaped portions 63 and a set of two trough-shaped portions 64. More or fewer crest-shaped portions 63 and trough-shaped portions 64 may be provided.

The plurality of alternating crest-shaped portions 63 and trough-shaped portions 64 of the first side 61 of the track 38 are substantially aligned with the plurality of alternating crest-shaped portions 63 and trough-shaped portions 64 of the second side 62 of the track 38. In this example, as shown in FIG. 6A, the plurality of trough-shaped portions 64 of the first side 61 of the track 38 are offset from the plurality of trough-shaped portions 64 of the second side 62 of the track 38 in a first direction by a first predetermined distance. In the example shown in FIG. 6A, the trough-shaped portions 64 of the first side 61 are offset in the first direction relative to the corresponding trough-shaped portions 64 of the second side 62 by distance d1 (e.g., to the left along a horizontal direction in FIG. 6A). Similarly, the plurality of crest-shaped portions 63 of the first side 61 of the track 38 are offset from the plurality of crest-shaped portions 63 of the second side 62 of the track 38 in a second direction opposite the first direction by a second predetermined distance. In the example shown in FIG. 6A, the crest-shaped portions 63 of the first side 61 are offset in the second direction relative to the corresponding crest-shaped portions 63 of the second side 62 by distance d2 (e.g., to the right along a horizontal direction in FIG. 6A). The offset d1 in the first direction and the offset d2 in the second direction are configured to allow the inner housing 31 to rotate in a first rotational direction (e.g., clockwise) and prevent the inner housing 31 from rotating in a second rotational direction opposite the first rotational direction (e.g., counterclockwise), as shown by FIG. 6B, discussed below.

FIG. 6B illustrates how the inner housing 31 rotates in a one-directional or unidirectional manner based on the configuration of the track 38. As discussed above, rotational movement of the inner housing 31 is initiated by either a spring force caused by the spring 32 of the airflow switching valve 6 or by air pressure caused by an inspiratory breath (i.e., airflow A) flowing into the airflow switching valve 6 from the mechanical ventilator 1.

Starting from an at rest position (e.g., an initial position), when the ventilator 1 is not generating and providing an inspiratory breath to the airflow switching valve 6, the spring 32 of the airflow switching valve 6 exerts a spring force (hereinafter denoted by Sf) on the inner housing 31, which causes the pegs 41 to be positioned in the trough-shaped portions 64 formed by the second side 62 of the track 38. The pegs 41 are captive in that at least parts of the pegs 41 may always be disposed within the track 38, between the first side 61 and second side 62 of the track 38 (e.g., within a channel partially formed by the first side 61 and the second side 62). This point in time is denoted in FIG. 6B by the position of the peg 41 in the left trough-shaped portion 64 (e.g., trough-shaped portion 64a of FIG. 6A).

When the ventilator 1 generates a first inspiratory breath for the first patient 8, an air pressure force Af1 from the first inspiratory breath is exerted on the closed portion 59 of the second space 56 in the second section 52 of the inner housing 31, and thus the pegs 41 of the inner housing 31. This air pressure force Af1 causes the pegs 41 to move upward (e.g., away from trough-shaped portions 64 and away from the open end 34 of the outer housing 30). As the pegs 41 contact the first side 61 of the track 38, the pegs 41 translate along the track 38 following the shape of the first side 61 of the track 38. This path of movement, which is denoted in FIG. 6B by P1, causes the inner housing 31 to rotate in a first direction (e.g., counterclockwise) by 90 degrees. Once the pegs 41 reach the crest-shaped portions 63, respectively, of the track 38, the inner housing 31 is in the first position, where one of the first openings 36 of the plurality of first openings 36, 37 of the outer housing 30 is aligned with one of the second openings 39 of the plurality of second openings 39, 40 of the inner housing 31. This point in time is denoted in FIG. 6B by the position of the peg 41 in the middle crest-shaped portion 63 (e.g., crest-shaped portion 63a of FIG. 6A). In this position, the airflow switching valve 6 is configured to provide the first inspiratory breath to the first patient 8.

When the ventilator 1 stops providing the first inspiratory breath, the pressure force Af1 from the first inspiratory breath is no longer present and the spring pressure force Sf1 causes the inner housing 31 to move downward (e.g., away from crest-shaped portions 63 and away from the closed end 33 of the outer housing 30). The pegs 41 move downward until the pegs 41 contact the second side 62 of the track 38, at which point the pegs 41 translate along the second side 62 of the track 38 following the shape of the second side 62 of the track 38. This path of movement, which is denoted in FIG. 6B by P2, causes the inner housing 31 to rotate in the first direction (e.g., counterclockwise) by another 90 degrees. Once the pegs 41 reach the trough-shaped portions 64 of the track 38, respectively, the inner housing 31 is in an intermediate position, where none of the plurality of first openings 36, 37 of the outer housing 30 are aligned with any of the plurality of second openings 39, 40 of the inner housing 31. This point in time is denoted in FIG. 6B by the position of the peg 41 in the right trough-shaped portion 64 (e.g., trough-shaped portion 64b of FIG. 6A). In this position, the airflow switching valve 6 is configured to prevent any airflow to either of the first patient 8 or second patient 9.

When the ventilator 1 generates a second inspiratory breath for the second patient 9 (i.e., the second breath generated by the ventilator 1, but the first breath provided to the second patient 9), an air pressure force Af2 from the second inspiratory breath is exerted on the inner housing 31 and thus the pegs 41 of the inner housing 31. This air pressure force Af2 causes the pegs 41 to move upward (e.g., away from trough-shaped portions 64 and away from the open end 34 of the outer housing 30). As the pegs 41 contact the first side 61 of the track 38, the pegs 41 translate along the track 38 following the shape of the first side 61 of the track 38. This path of movement, which is denoted in FIG. 6B by P3, causes the inner housing 31 to rotate in the first direction (e.g., counterclockwise) by another 90 degrees. Once the pegs 41 reach the crest-shaped portions 63 of the track 38, the inner housing 31 is in the second position, where another of the first openings 37 of the plurality of first openings 36, 37 of the outer housing 30 is aligned with another of the second openings 40 of the plurality of second openings 39, 40 of the inner housing 31. This point in time is denoted in FIG. 6B by the position of the peg 41 in the right most crest-shaped portion 63 (e.g., crest-shaped portion 63b of FIG. 6A). In this position, the airflow switching valve 6 is configured to provide the second inspiratory breath to the second patient 9.

When the ventilator 1 stops providing the second inspiratory breath, the pressure force Af2 from the second inspiratory breath is no longer present and the spring pressure force Sf2 causes the inner housing 31 to move downward (e.g., away from crest-shaped portions 63 and away from the closed end 33 of the outer housing 30). The pegs 41 move downward until the pegs 41 contact the second side 62 of the track 38; at this point, the pegs 41 translate along the second side 62 of the track 38 following the shape of the second side 62 of the track 38. This path of movement, which is denoted in FIG. 6B by P4, causes the inner housing 31 to rotate in the first direction (e.g., counterclockwise) by another 90 degrees. Once the pegs 41 reach the trough-shaped portions 64 of the track 38, the inner housing 31 is back at the starting position (e.g., the initial position, which is an intermediate position), where the airflow switching valve 6 is configured to prevent any airflow to either of the first patient 8 or second patient 9.

As shown above, the unique design and configuration of the track 38 with the pegs 41 allows the inner housing 31 to sequentially rotate in an alternating fashion between various airflow (breath state) and non-airflow (non-breath state) positions.

In one embodiment, as shown above, the inner housing 31 is configured to rotate 90 degrees between each position. Thus, the inner housing 31 rotates 180 degrees between the first position and the second position, and 180 degrees between the two intermediate positions. In this example, the plurality of second openings 39, 40 are 180 degrees apart (i.e., on opposite sides of the inner housing 31), as described above. Other configurations are possible. For example, as will be discussed below with respect to FIGS. 8A-8C and 9A-9B, the wave shape 60 track 38 may include additional crest-shaped portions 63 and trough-shaped portions 64. In this case, the inner housing 31 may be configured to only rotate 45 degrees between each position, resulting in a 90-degree rotation between breath positions instead of 180 degrees. In this case, the number of second openings may change (e.g., increase). The position and spacing of the second openings may also change accordingly (i.e., 90 degrees apart rather than 180 degrees apart), which may correspond to additional first openings or the same number of first openings.

Figure 7A:
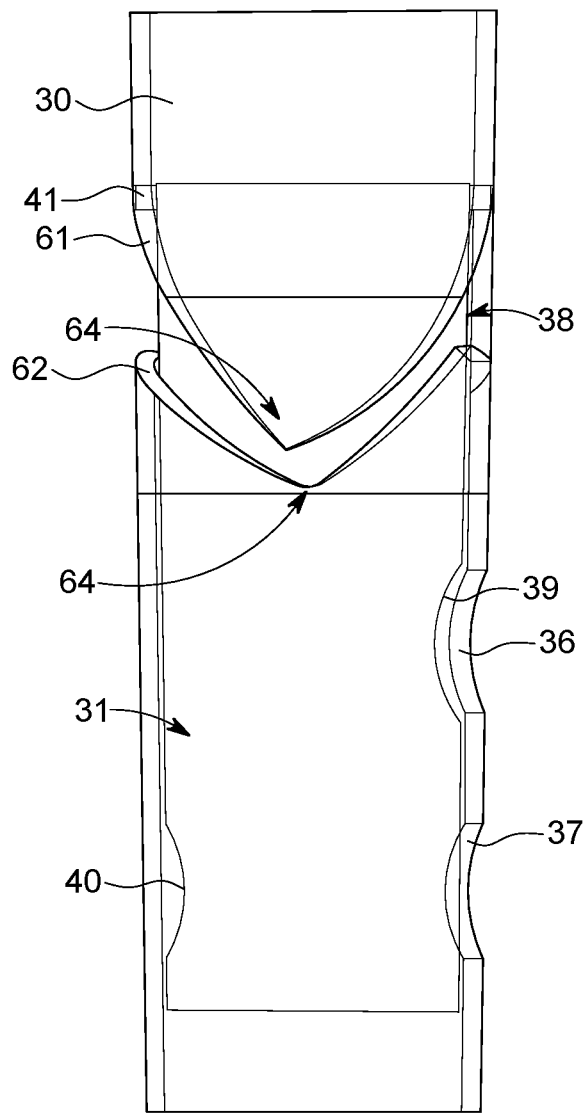
FIGS. 7A-7C show one embodiment of a first airflow position of the inner housing of FIGS. 5A-5B inside the outer housing of FIG. 4.
Figure 7B:
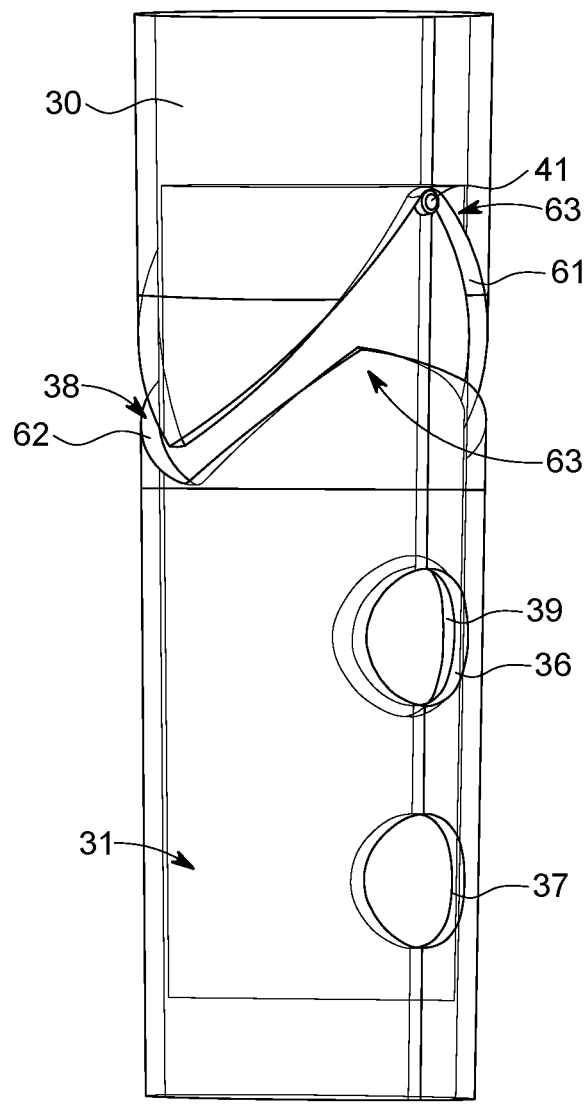
Figure 7C:
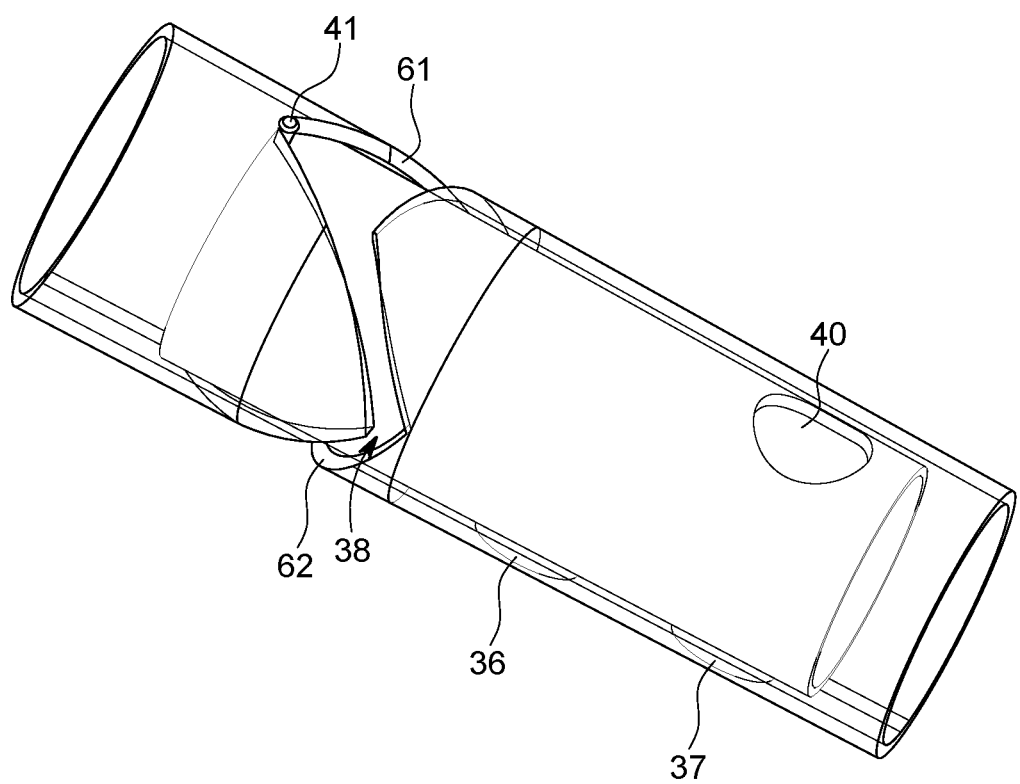

FIGS. 7A-7C show one embodiment of a first airflow position of the inner housing 31 of FIGS. 5A-5B inside the outer housing 30 of FIG. 4. As shown in FIGS. 7A-7C, one of the first openings 36 of the plurality of first openings 36, 37 of the outer housing 30 is aligned with one of the second openings 39 of the plurality of second openings 39, 40 of the inner housing 31. In this position, the pegs 41 are positioned in the crest-shaped portions 63 of the track 38. FIGS. 7A and 7C also show how another of the second openings 40 is not aligned with any first opening. FIG. 7A shows how the second openings 39, 40 are positioned on opposite sides of the inner housing 31 (i.e., 180 degrees apart). In this position, the airflow switching valve 6 is configured to provide the first inspiratory breath to the first patient 8.

Figure 8A:
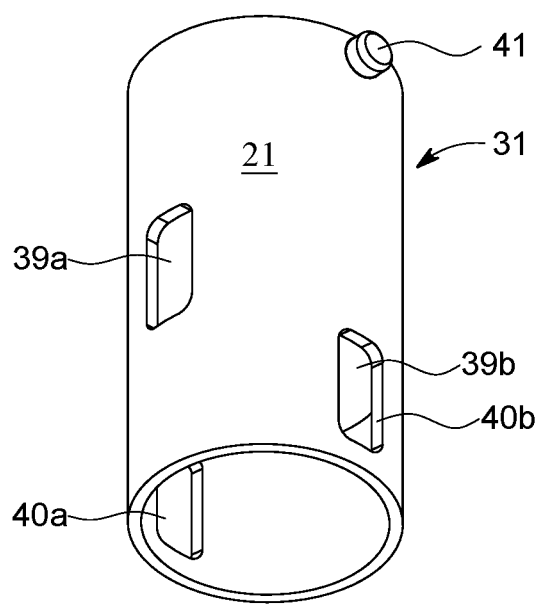
FIG. 8A illustrates another embodiment of an inner housing of the airflow switching valve of FIG. 3.

FIG. 8A illustrates another embodiment of an inner housing 31 of the airflow switching valve. As shown in FIG. 8A, the plurality of second openings 39, 40 of the inner housing 31 includes two sets of second openings 39a-39b, 40a-40b. A first set of second openings includes second openings 39a and 39b. A second set of second openings includes second openings 40a and 40b. In this embodiment, each set of second openings 39a-39b, 40a-40b includes a pair of second openings arranged on opposite sides of the inner housing 31 from each other (e.g., 180 degrees apart). In this example, the first set of second openings 39a, 39b is positioned proximate the closed portion 59 of the second space 56 of the second section 52 of the inner housing 31. The second set of the second openings 40a, 40b is positioned proximate the open portion 58 of the second space 56 of the second section 52 of the inner housing 31. Thus, the first set of second openings 39a, 39b is offset from the second set of second openings 40a, 40b along the direction of the rotational axis 42 (i.e., along the length of the inner housing 31). The first set of second openings 39a, 39b is also offset from the second set of second openings 40a, 40b in a transverse direction to the rotational axis 42. In one embodiment, this transverse offset is a 90-degree offset.

Figures 8B, 8C:
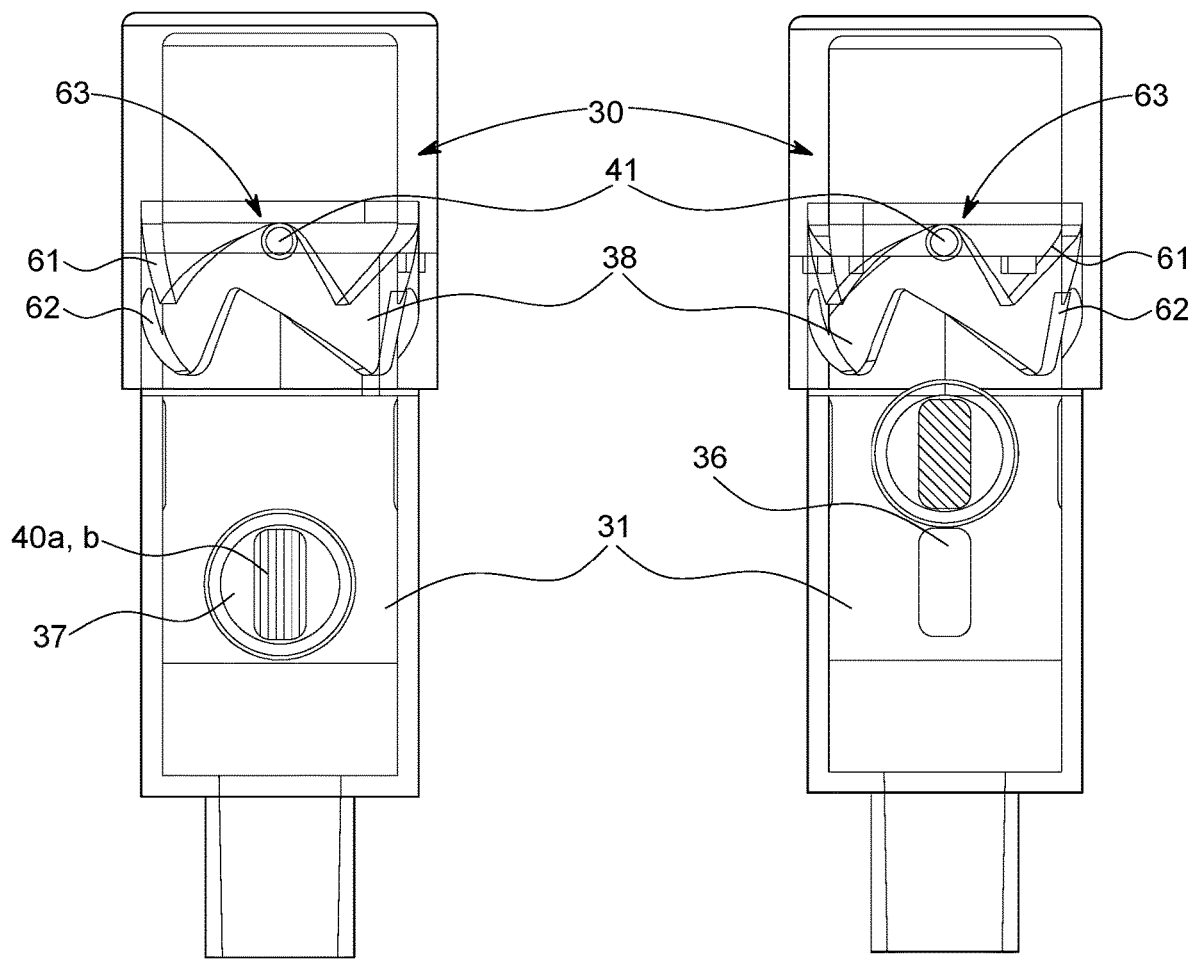
FIGS. 8B-8C show one embodiment of a second airflow position of the inner housing of FIG. 8A inside another embodiment of an outer housing of the airflow switching valve of FIG. 3.

FIGS. 8B-8C show one embodiment of a second airflow position of the inner housing 31 of FIG. 8A inside another embodiment of an outer housing 30. The outer housing 30 of FIGS. 8B and 8C is similar to the outer housings described above, except that in this embodiment, the plurality of first openings 36, 37 are arranged opposite each other and the track 38 includes additional crest-shaped portions 63 and trough-shaped portions 64. Hoses that attach to the plurality of first openings 36, 37 of the outer housing 30 may have large diameter filters, which may cause the hoses to interfere with each other. Thus, by arranging the plurality of first openings 36, 37 on opposite sides of each other, hose interference may be prevented. In this case, the inner housing 31 is configured to rotate 45 degrees along the track 38 between each position, resulting in a 90-degree rotation between breath positions instead of 180 degrees as described above, which is due to the additional second openings, described above with respect to FIG. 8A. Reducing the movement along the track 38 requires less movement overall and is more efficient.

FIGS. 8B and 8C illustrate the same airflow position (e.g., second airflow position) but from opposite sides of the airflow switching valve (e.g., 180-degree difference in viewpoint). As shown in FIG. 8B, another first opening 37 of the plurality of first openings 36, 37 of the outer housing 30 is aligned with another second opening 40a or 40b of the plurality of second openings 39, 40 of the inner housing 31. As shown in FIGS. 8B and 8C, in the second airflow position, the pegs 41 are positioned in the crest-shaped portions 63 of the track 38. In this position, the airflow switching valve 6 is configured to provide the second inspiratory breath to the second patient 9. As shown in FIG. 8C, the first opening 36 disposed proximate the track 38 of the outer housing 30 is not aligned with any second opening of the plurality of second openings 39, 40, and thus airflow is prevented from flowing out of that first opening 36 to the first patient 8.

Figures 9A, 9B:
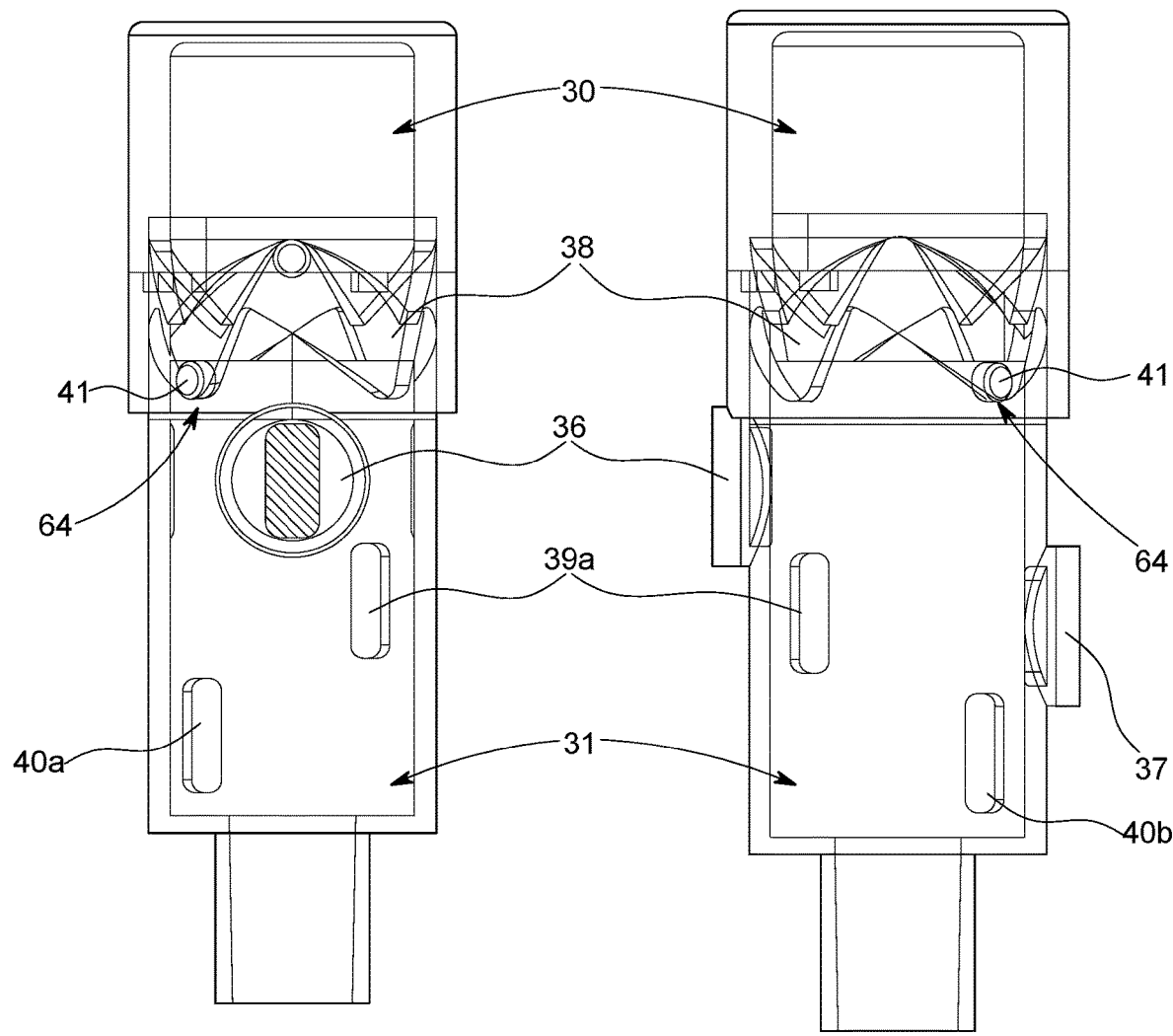
FIGS. 9A-9B show one embodiment of an intermediate position of the inner housing of FIG. 8A inside the outer housing of FIGS. 8B-8C.

FIGS. 9A-9B show one embodiment of an intermediate position of the inner housing 31 of FIG. 8A inside the outer housing 30 of FIGS. 8B and 8C. As shown in FIGS. 9A-9B, the pegs 41 are positioned in the trough-shaped portions 64 of the track 38. In this position, none of the plurality of first openings 36, 37 of the outer housing 30 are aligned with any of the plurality of second openings 39a, 39b, 40a, 40b of the inner housing 31. In this position, the airflow switching valve 6 is configured to prevent any airflow to either of the first patient 8 or second patient 9.

Figure 10:
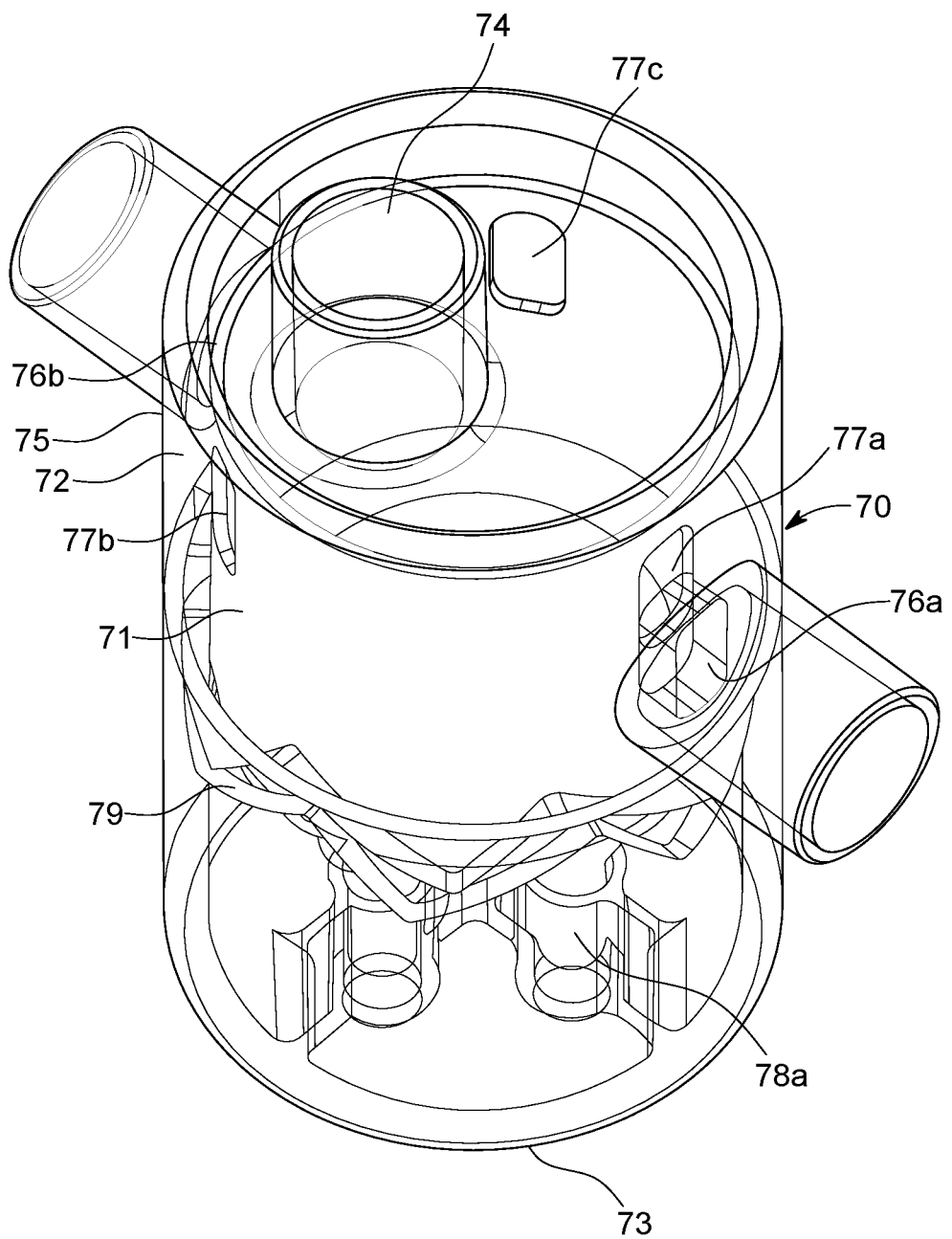
FIG. 10 illustrates another embodiment of an airflow switching valve.

FIG. 10 illustrates another embodiment of the airflow switching valve 6. The airflow switching valve 6 includes an outer housing 70 and inner housing 71. The outer housing includes a first end 73, a second end 74 and a first wall 75. The first wall at least partially defines a first volume 72. The outer housing 70 includes two first opening 76a, 76b. The second end comprises an inflow port 74 configured to be coupled to tubing, such as inspiratory hose 4 of FIG. 2. The inner housing 71 is disposed within the first volume 72. In one embodiment, the inner housing 71 is a piston. The inner housing 71 includes three second openings 77a, 77b and 77c at 120-degree angle. The inner housing 71 (e.g., including a body of the inner housing 71a) is rotatable and translatable within the outer housing 70 in order to move (e.g., rotate and translate) into different positions. The movement of the inner housing within the outer housing (e.g., rotational movement and/or translational movement) is guided by a track 79 of the outer housing. Extensions (e.g., pins, pegs, and the like) on the inner housing are at least partially disposed and translatable within the track 79 of the outer housing 70, thereby directing the movement of the inner housing between varying positions within the outer housing. The plurality of positions includes a first airflow position, a second airflow position and intermediate position. The illustrated embodiment is in first airflow position wherein the first opening 76a and second opening 77a align to allow to provide airflow from the single ventilator to a first patient.

The airflow switching valve in accordance with said embodiment comprises plurality of guide tubes 78a. Each of the plurality of guide tubes 78a is adapted to receive a spring. In a preferred embodiment, total guide tubes 78a are four.

Figure 11A:
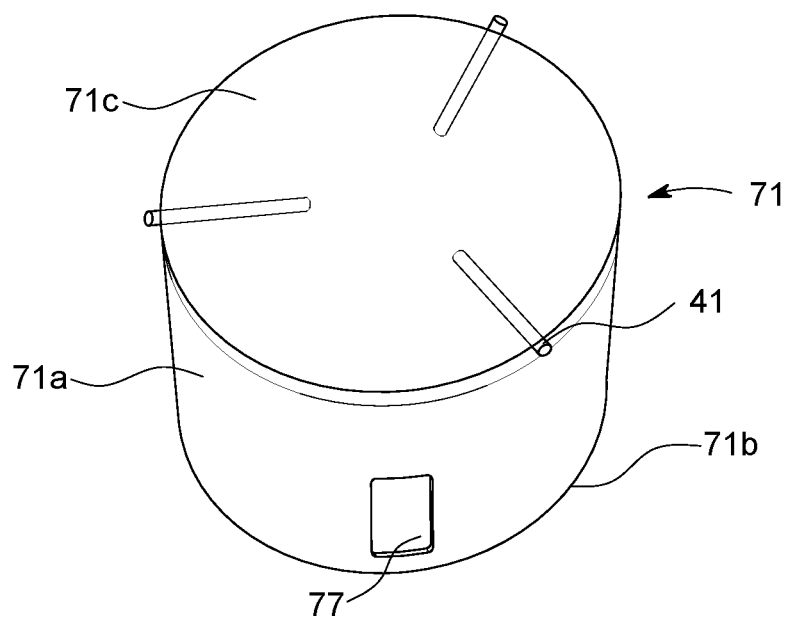
FIGS. 11a-11d show unassembled perspective view of another embodiment of an airflow switching valve.

FIG. 11a-11d illustrates an unassembled perspective view of another embodiment of an airflow switching valve 6 similar to FIG. 10 but with three first openings. FIG. 11a illustrates the inner housing 71. The inner housing 71 includes a plurality of second openings (e.g., apertures) 77 in the surface of body 71a of the inner housing 71. The body has a first end 71b and a second end 71c. In one embodiment, the first end 71b is an open end and the second end 71c is closed. The inner housing 71 (e.g., including a body of the inner housing 71a) is rotatable and translatable within the outer housing 70 in order to move (e.g., rotate and translate) into different positions. The movement of the inner housing within the outer housing (e.g., rotational movement and/or translational movement) is guided by a track 79 of the outer housing. Extensions 41 on the inner housing engage a guide (e.g., a track) of the outer housing and translate along the track, thereby directing the movement of the inner housing between varying positions within the outer housing. Movement of the inner housing 71 is initiated by either a spring force caused by the spring of the airflow switching valve or by air pressure caused by an inspiratory breath flowing into the airflow switching valve from the mechanical ventilator as explained in detail above.

Figure 11B:
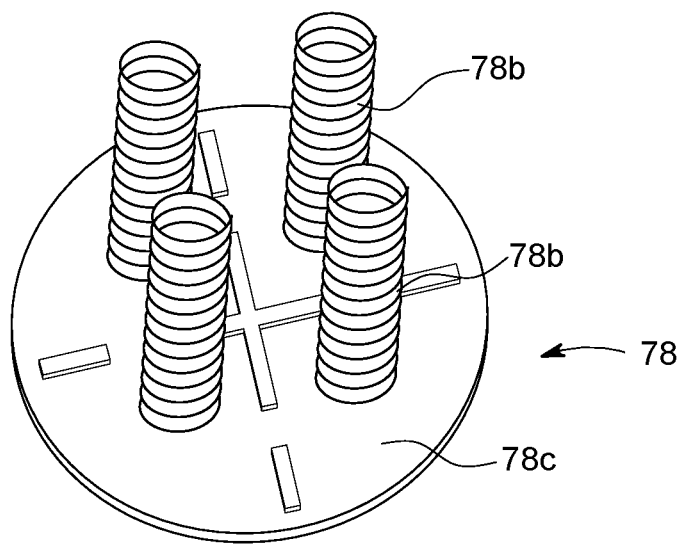
Figure 11C:
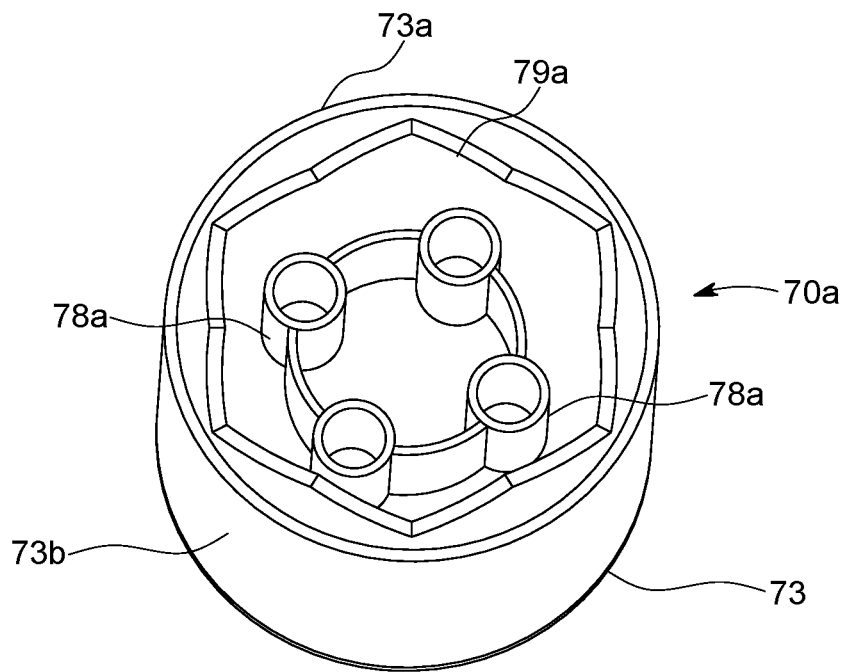

FIG. 11b illustrates a spring holder 78 comprising of a surface 78c adapted to hold plurality of springs 78b. FIG. 11c illustrates top part 70a of the outer housing 70. The top part 70a comprises of a first end 73, a second end 73a and a body 73b. In a preferred embodiment, the first end 73 is closed and the second end 73a is open. The top part 70a also comprises of plurality of guide tubes 78a adapted to receive the plurality of springs 78b. The guide tubes 78a are secured on the inner side of first end 73 and provide a channel for the springs to extend and cause the inner housing 71 to rotate into plurality of positions within the track 79 as explained in detail above. The springs expand between walls 73 and 78c.

The wall 78c also provides a closed wall on which the wall 71c of the inner housing 71 is placed.

The track 79 comprises of opposing sawtooth tracks 79a and 79b. The top sawtooth track 79a is in or on the body 73b and the bottom sawtooth track is or on the body 74c. The track 79 traps the extensions 41 between the two track 79a and 79b and moves in different positions i.e., a first airflow position, a second airflow position, a third air flow position and intermediate position as explained in detail above. The air flow raises the inner housing 71 where it hits the top track 79a and spins a fixed amount until it hits a peak but when the air flow ends the piston drops forced down by the springs but to make sure it continues in the correct direction (i.e., toward the next air flow position) and cannot go backwards. The lower track 79b it will follow is offset behind the upper peak so it has to catch the pins and go the right way. Conversely the top track is such that it is offset to ensure it turns the correct way on the upstroke.

Figure 11D:
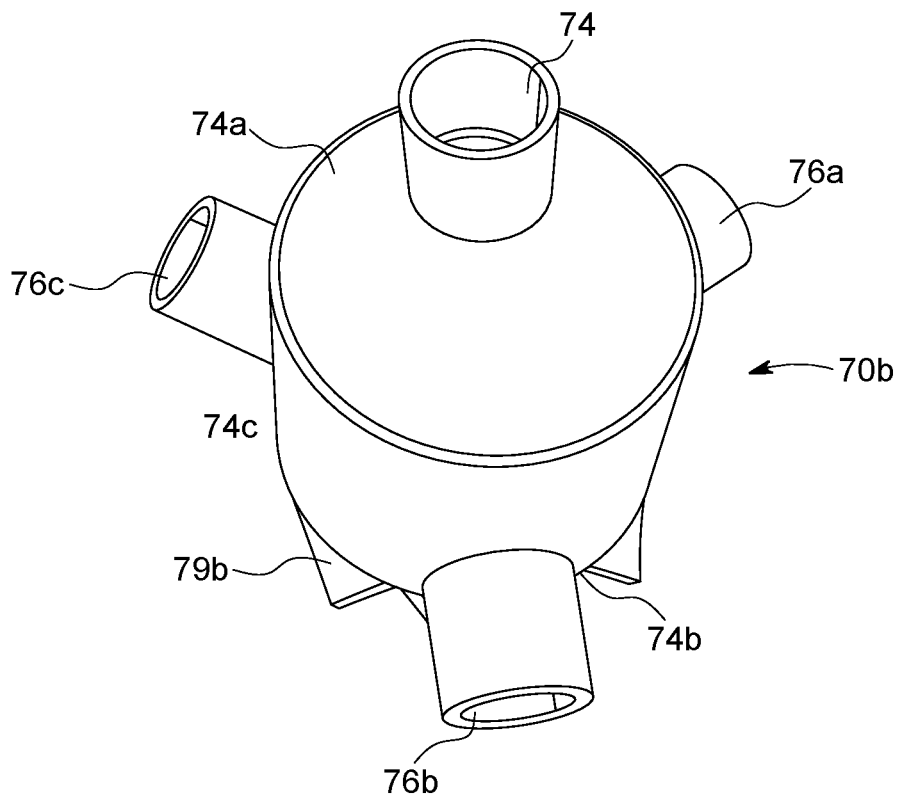

FIG. 11d illustrates the bottom part 70b of the outer housing 70. The bottom part comprises of a top end 74a and a bottom end 74b. The top end 74a comprises an inflow port 74 configured to be coupled to tubing, such as inspiratory hose 4 of FIG. 2 to receive a positive pressure flow of gases, such as oxygen, from the mechanical ventilator 1. The bottom part 74b comprising the bottom track 79b in or the body 74c. The top end 76c comprises of three first opening 76a, 76b and 76c thereby allowing ventilating three patients sequentially.

Figure 12A:
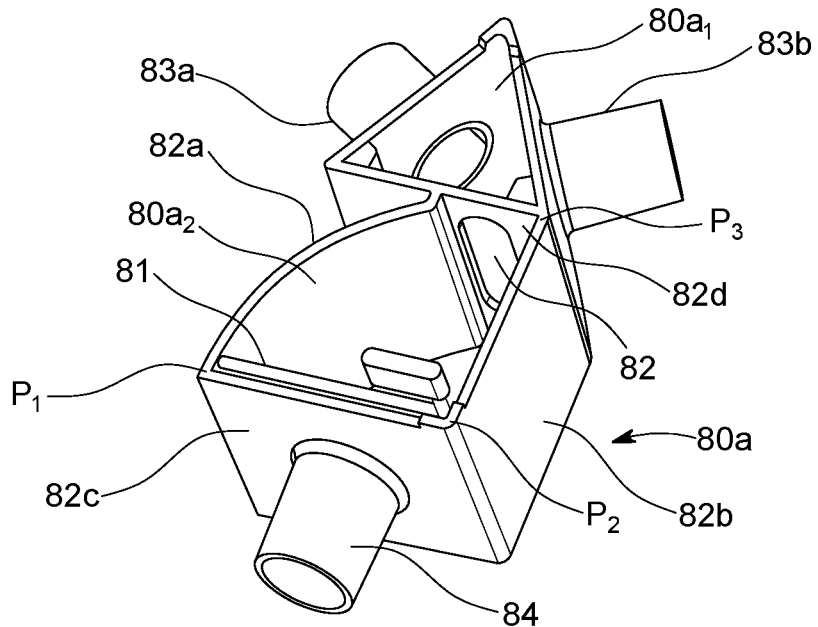
FIGS. 12a-12c illustrate another embodiment of inner housing of an airflow switching valve.
Figure 12B:
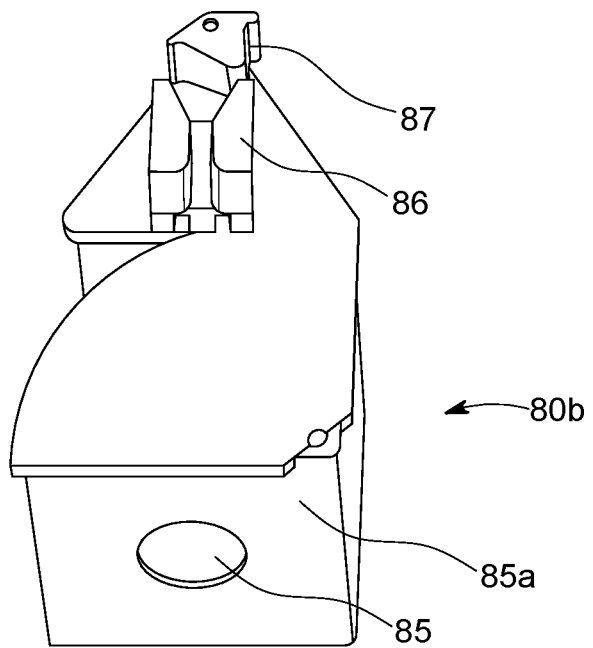
Figure 12C:
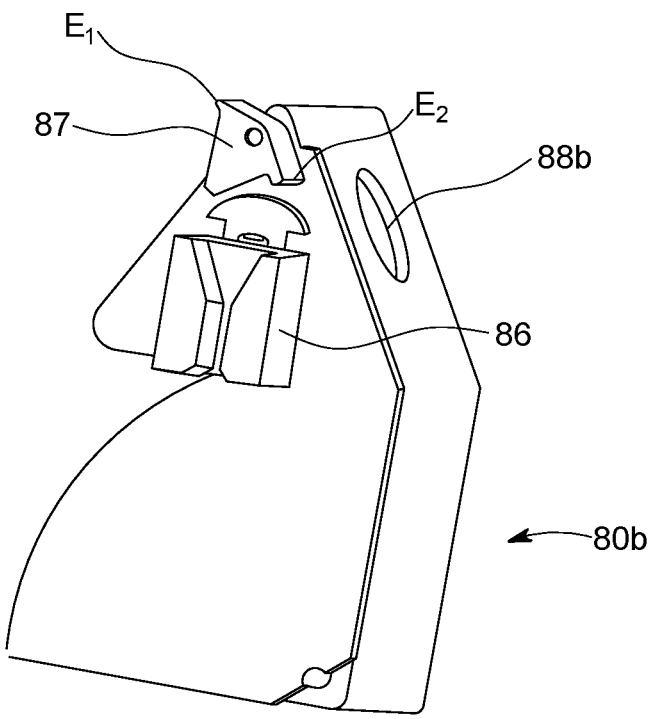

FIG. 12a-12c illustrates perspective view of another embodiment of the air flow switching valve. FIG. 12a illustrates left portion 80a and FIGS. 12b and 12c illustrate the right portion 80b of the inner housing 80. The inner housing 80 is disposed within an outer housing (not shown).

The left portion 80a comprises of a top chamber $80a_1$ and a bottom chamber $80a_2$. The bottom chamber comprises of a left wall 82a, a right wall 82b, a bottom wall 82c and a top wall 82d. The bottom chamber $80a_2$ comprises an opening 84 on the bottom wall 82c allowing airflow from the inspiratory hose 4 of FIG. 2 to enter the bottom chamber $80a_2$. The bottom chamber $80a_1$ also comprises of a flow door 81 that cover the said air inlet and is adapted to pivot between the bottom wall 82c and top wall 82d. The top wall 82d comprises of an opening 82 to allow the airflow to enter the second chamber $80a_1$. The top chamber $80a_1$ comprises two air outlets 83a and 83b to ventilate two patients sequentially. The number of air outlet are not limited.

FIGS. 12b and 12c refers to right portion 80b of the inner housing 80. The right portion 80b comprises an air inlet 85 in a bottom wall 85a. The cross-section of the opening 85 corresponds to that of the opening 84 in order to allow the air to flow through the opening 84 and 85 when the left portion 80a and 80b are assembled to form the inner housing. The right portion 80b comprises of an actuator (not shown) secured in a guide 86. As pressurized airflow (e.g., pressurized inspiratory breath generated by the ventilator) enters through the openings 84 and 85, the flow door moves from position P1, P2 to position P3, P2 to allow the pressurized air to flow to second chamber $80a_1$ through opening 82. In this transition of position, the flow door 85 actuates the actuator that glides through the guide 86 and engage with the diverter to flip it from position PD1 (as shown in FIG. 12b) to position PD2 (as shown in FIG. 12c). The actuators locks and turns alternatively with end E1 and E2. The flipping of the diverter 86 opens alternatively the openings 88a (not shown) and 88b to sequentially allow the air to flow from either 83a or 83b to ventilate two patients.

Figure 13:
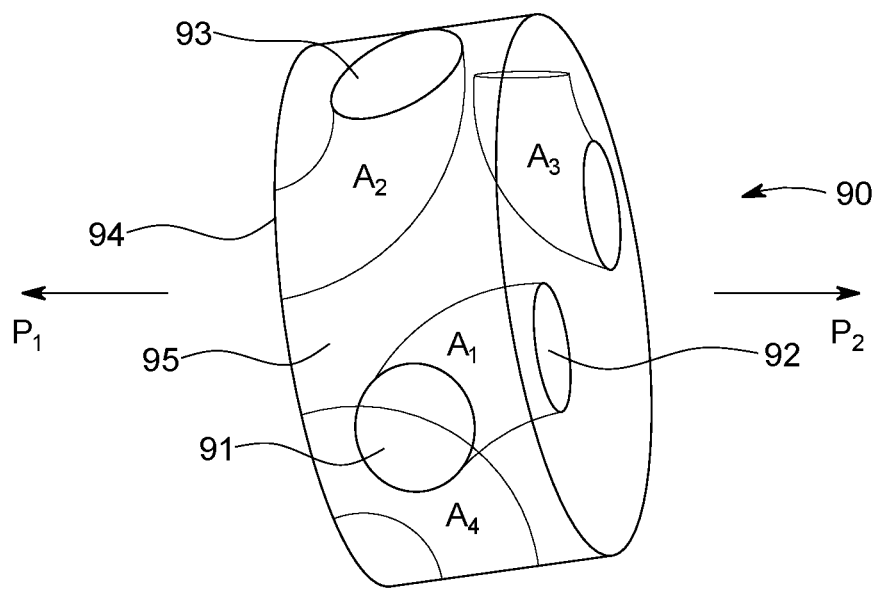
FIG. 13 illustrate another embodiment of inner housing of an airflow switching valve.

FIG. 13 illustrate another embodiment of the air flow switching valve. The air flow switching valve comprises an outer housing (not shown) and an inner housing 90 preferably disk shaped. The inner housing 90 comprises plurality of air tunnels. In said embodiment, the inner housing comprises of four air tunnels A1, A2, A3, A4. The number of air tunnels is not limited. The outer housing comprises an opening to allow pressurized airflow (e.g., pressurized inspiratory breath generated by the ventilator) to enter. The outer housing comprises of a cam assembly to hold, align and rotate the inner housing 90. The cam assembly (not shown) holds the inner housing 90 such that wall 95 of the inner housing aligns linearly with the opening on the outer chamber. In said embodiment, there are four air tunnels at 90 degrees. As pressurized airflow (e.g., pressurized inspiratory breath generated by the ventilator) enters through the outer housing it enters the inner housing 90 through opening 91 of the air tunnel A1 and exist through an opening 92 to a patient P2. The cam assembly then makes the inner housing 90 to turn 90 degrees aligning opening 93 of air tunnel A2 with the opening of the outer housing. Thereby allowing air to enter through opening 93 and exiting through opening 94 of air tunnel A2 to patient P1. Thereby sequentially ventilating two patients.

Referring back to FIG. 2, a shared ventilatory mode system operable to provide artificial respiration to at least two patients 8, 9 using a single ventilator is disclosed. The shared ventilatory mode system includes a mechanical ventilator 1, an airflow switching valve 6, at least two patient interfaces 10, 11, at least two one-way valves 7, and an air circuit 15 connecting the mechanical ventilator 1, the airflow switching valve 6, and the at least two one-way valves 7 to the at least two patient interfaces 10, 11, such that the shared ventilatory mode system is operable to provide a breathable gas to the at least two patients 8, 9.

The airflow switching valve 6 of the shared ventilatory mode system may be designed and configured the same as the airflow switching valve 6 disclosed above with regard to FIGS. 3-13. In this embodiment airflow switching valve of FIG. 3-9 is considered. As discussed above, the airflow switching valve 6 includes an outer housing 30 and an inner housing 31 disposed inside the outer housing 30. The outer housing 30 includes a plurality of first apertures 36, 37 and a track 38. The inner housing 31 includes a plurality of second apertures 39, 40 and a plurality of extensions 41. The plurality of extensions 41 are designed and configured the same as the extensions 41 discussed above. The plurality of extensions 41 are configured to translate within the track 38 of the outer housing 30 to rotate the inner housing 31 between a plurality of positions.

The mechanical ventilator 1 is operable to generate an inspiratory breath containing the breathable gas to the air circuit 15. The breathable gas may contain oxygen and other gases.

The air circuit 15 is operable to transfer the inspiratory breath from the mechanical ventilator 1 to the airflow switching valve 6. The air circuit 15 is also operable to transfer the inspiratory breath from the airflow switching valve 6 to the at least two patient interfaces 10, 11 in an alternating manner depending on a position of the plurality of positions of the inner housing 31 inside the outer housing 30 of the airflow switching valve 6. In this way, only a single patient interface of the at least two patient interfaces 10,11 receives the inspiratory breath. Thus, only one lung (or set of lungs) 12, 13 from only one patient 8, 9 receives the inspiratory breath. The air circuit 15 is operable to transfer an expiratory breath from a patient interface of the at least two patient interfaces 10, 11 to the at least two one-way valves 7. The air circuit 15 is also operable to transfer the expiratory breath from the at least two one-way valves 7 to the mechanical ventilator 1.

In one embodiment, the airflow switching valve 6 is operable to provide the breathable gas from the mechanical ventilator 1 to a first patient 8 of the at least two patients 8, 9 when the inner housing 31 is in a first position of the plurality of positions. The airflow switching valve 6 is also operable to provide the breathable gas to a second patient 9 of the at least two patients 8, 9 when the inner housing 31 is in a second position of the plurality of positions. In this embodiment, one first aperture 36 of the plurality of first apertures 36, 37 of the outer housing 30 is aligned with one second aperture 39 of the plurality of second apertures 39, 40 of the inner housing 31 in the first position. Further, another first aperture 37 of the plurality of first apertures 36, 37 of the outer housing 30 is aligned with another second aperture 40 of the plurality of second apertures 39, 40 of the inner housing 31 in the second position.

Figure 14:
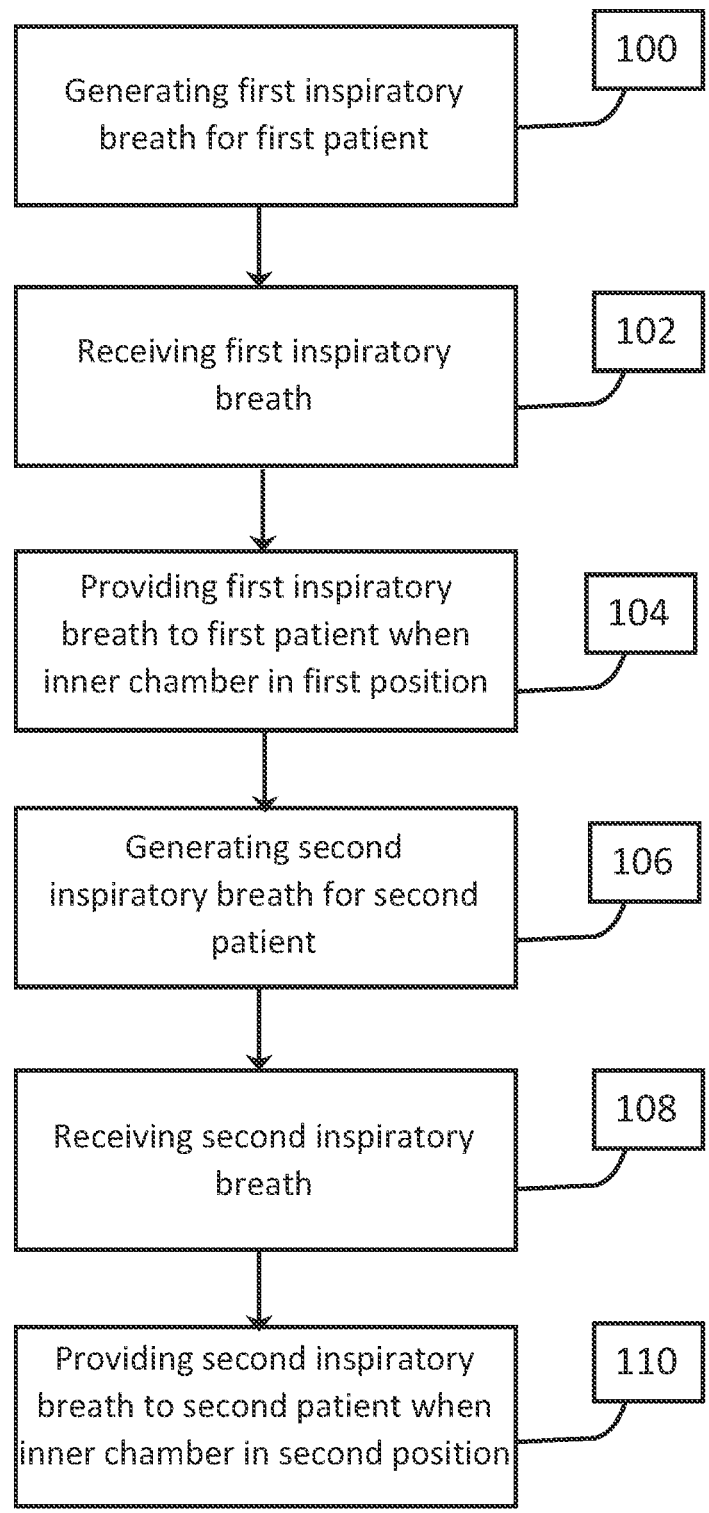
FIG. 14 shows a flowchart of one embodiment of a method for providing inspiratory breaths to multiple patients sharing a single ventilator on an artificial breathing system.

FIG. 14 shows a flowchart of one embodiment of a method for providing inspiratory breaths to multiple patients sharing a single ventilator on an artificial breathing system. The method may be performed using the airflow switching valve 6 shown in FIGS. 2-13 but for this example airflow switching valve of FIGS. 2-9B is used for explanation. The method is implemented in the order shown, but other orders may be used. Additional, different, or fewer acts may be provided. Similar methods may be used for providing inspiratory breaths to multiple patients sharing a single ventilator on an artificial breathing system.

The artificial breathing system includes an airflow switching valve. The airflow switching valve includes an outer housing and an inner housing. The outer housing includes a plurality of first apertures and a track. The inner housing includes a plurality of second apertures and a plurality of extensions. The plurality of extensions are configured to translate within the track of the outer housing to rotate the inner housing between a plurality of positions. In one embodiment, the outer housing includes the plurality of second apertures and the plurality of extensions, and the inner housing includes the plurality of first apertures and the track.

In act 100, a first inspiratory breath for a first patient of the multiple patients is generated by the single ventilator. The single ventilator may be a mechanical ventilator, such as the mechanical ventilator 1 discussed above. The first inspiratory breath may contain a breathable gas, such as oxygen, and may be introduced into an air circuit, such as the air circuit 15 discussed above, through an inspiratory port of the single ventilator.

In act 102, the first inspiratory breath is received by the airflow switching valve. The first inspiratory breath enters an airflow inlet of the inner housing of the airflow switching valve and the air pressure of the first inspiratory breath forces the inner housing further into the outer housing (e.g., away from the airflow inlet). This causes the plurality of extensions of the inner housing to engage with the track of the outer housing, which in turn causes the inner housing to rotate within the outer housing. As the inner housing rotates, one second aperture of the plurality of second apertures of the inner housing aligns with one first aperture of the plurality of first apertures of the outer housing. Once this alignment occurs, the airflow switching valve is in a first position of the plurality of positions.

In act 104, the first inspiratory breath is provided to the first patient of the multiple patients by the airflow switching valve when the inner housing is in the first position of the plurality of positions. The first inspiratory breath flows out of the aligned second and first apertures of the inner and outer housings, respectively, and flows through the air circuit to a patient interface device of the first patient. The first inspiratory breath is then provided to the lung or lungs of the first patient via the patient interface device.

Once the first inspiratory breath is provided to the first patient and there is no more air pressure forcing the inner housing into the outer housing, a spring or other counter force is exerted on the inner housing and forces the inner housing in an opposite direction (e.g., toward the airflow inlet). This once again causes the plurality of extensions of the inner housing to engage with the track of the outer housing and causes the inner housing to rotate within the outer housing. As the inner housing rotates, the aligned second and first apertures of the inner and outer housings, respectively, rotate out of alignment and airflow is prevented from flowing through the airflow switching valve. In this configuration, the airflow switching valve is in an intermediate position of the plurality of positions.

In act 106, a second inspiratory breath for a second patient of the multiple patients is generated by the single ventilator. The second inspiratory breath may be the second breath generated by the ventilator, but the second inspiratory breath is the first breath received by the second patient. Similar to the first inspiratory breath, the second inspiratory breath is introduced into the air circuit through the inspiratory port of the single ventilator to the airflow switching valve.

In act 108, the second inspiratory breath is received by the airflow switching valve. The second inspiratory breath enters the airflow inlet of the inner housing of the airflow switching valve and the air pressure of the second inspiratory breath forces the inner housing further into the outer housing (e.g., away from the airflow inlet). This once again causes the plurality of extensions of the inner housing to engage with the track of the outer housing, which in turn causes the inner housing to rotate within the outer housing. As the inner housing rotates, another second aperture of the plurality of second apertures of the inner housing aligns with another first aperture of the plurality of first apertures of the outer housing. Once this second alignment occurs, the airflow switching valve is in a second position of the plurality of positions.

In act 110, the second inspiratory breath is provided to the second patient of the multiple patients by the airflow switching valve when the inner housing is in the second position of the plurality of positions. The second inspiratory breath flows out of the second set of aligned second and first apertures of the inner and outer housings, respectively, and flows through the air circuit to a second patient interface device connected to the second patient. The second inspiratory breath is then provided to the lung or lungs of the second patient via the second patient interface device.

Once the second inspiratory breath is provided to the second patient and there is no more air pressure forcing the inner housing into the outer housing, the spring or other counter force is exerted on the inner housing and forces the inner housing in an opposite direction (i.e., towards the airflow inlet). This once again causes the plurality of extensions of the inner chamber to engage with the track of the outer housing and causes the inner housing to rotate within the outer housing once more. As the inner housing rotates, the second set of aligned second and first apertures of the inner and outer housings, respectively, rotate out of alignment and airflow is prevented from flowing through the airflow switching valve. In this configuration, the airflow switching valve is in another intermediate position of the plurality of positions.

In a further act, acts 100, 102, and 104 may be repeated and another inspiratory breath may be provided to the first patient after the completion of acts 106, 108, and 110.

As discussed above, the airflow switching valve may include a spring positioned between the outer housing and the inner housing. The spring may be compressed in a breath state and extended in a non-breath state. The breath state is when the airflow switching valve receives the first inspiratory breath or the second inspiratory breath. The non-breath state is when the airflow switching valve is not receiving the first inspiratory breath or the second inspiratory breath.

In this embodiment, receiving the first inspiratory breath causes the inner housing to compress the spring and simultaneously rotate into the first position by way of the plurality of extensions translating within the track of the outer housing. After providing the first inspiratory breath to the first patient, the spring is configured to extend and cause the inner housing to rotate into an intermediate position by way of the plurality of extensions translating within the track of the outer housing. The intermediate position is between the first position and the second position. Receiving the second inspiratory breath causes the inner housing to compress the spring and simultaneously rotate into the second position by way of the plurality of extensions translating within the track of the outer housing. After providing the second inspiratory breath to the second patient, the spring is configured to extend and cause the inner housing to rotate into another intermediate position by way of the plurality of extensions translating within the track of the outer housing. The other intermediate position is between the second position and the first position.

The present embodiments solve the above-described problem with a plurality of methods using a flow switching valve, a setup system of ventilator hoses 4,5, and control settings on the mechanical ventilator, which facilitate the safe ventilation of two or more patients 8, 9 with the use of one mechanical ventilator 1 (e.g., a shared ventilator mode).

It is an advantage of the present invention, that a single ventilator can be used to ventilate multiple patients. The airflow switching valve, system and methods thereby increases the ventilating capacity in a cost effectively manner.

It is an advantage of the invention, that the response time of a health facility in emergency situations such as an epidemic, pandemic etc. can be reduced drastically. Ventilators are not only expensive, but the time of procurement, installation and training is also extremely high. Therefore, during emergency situations the present invention is of acute importance.

While the present disclosure has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The above description does not provide specific details of manufacture or design of the various components. Those of skill in the art are familiar with such details, and unless departures from those techniques are set out, techniques, known, related art or later developed designs and materials should be employed. Those in the art are capable of choosing suitable manufacturing and design details.

The claims, as originally presented and as they may be amended, encompass variations, alternatives, modifications, improvements, equivalents, and substantial equivalents of the embodiments and teachings disclosed herein, including those that are presently unforeseen or unappreciated, and that, for example, may arise from applicants/patentees and others.

The invention claimed is:

1. An airflow switching valve for use with a single ventilator for ventilating two or more patients, the valve comprising:
    an outer housing having a plurality of first openings; and
    an inner housing having a plurality of second openings,
        wherein a pressurized airflow from the ventilator moves the inner housing along a track to align a second opening from the plurality of second opening with a first opening from the plurality of first openings to sequentially ventilate the two or more patients.

2. The airflow switching valve of claim 1, wherein,
    the outer housing comprises:
        a first end and a second end;
        a first wall extending between the first end and the second end of the outer housing, the first wall partially defining a first volume;
        a second wall connected to the first wall, the second wall being at or adjacent to the first end of the outer housing and forming a closed end of the outer housing; and
        the track in or on the first wall;
        wherein the plurality of first openings are on the first wall;
    the inner housing disposed within the first volume comprising:
        a body; and
        a plurality of extensions extending away from a surface of the body, the plurality of extensions being at least partially disposed and translatable within the track;
        wherein the plurality of second openings are on the surface of the body;
    a spring disposed within the first volume, the spring extending between the closed end of the outer housing and the inner housing.

3. The airflow switching valve of claim 2, wherein the inner housing is rotatable relative to the outer housing about an axis of rotation, between a plurality of positions to sequentially ventilate the two or more patients, and
    wherein a shape of the track defines the plurality of positions.

4. The airflow switching valve of claim 3, wherein the plurality of positions comprises:
    a first airflow position, in which one first opening of the plurality of first openings through the first wall of the outer housing is aligned with one second opening of the plurality of second openings through the surface of the body of the inner housing; and
    a second airflow position, in which another first opening of the plurality of first openings through the first wall of the outer housing is aligned with another second opening of the plurality of second openings through the surface of the body of the inner housing.

5. The airflow switching valve of claim 4, wherein the airflow switching valve is operable to provide airflow from the single ventilator to a first patient when the inner housing is in the first airflow position, and the airflow switching valve is operable to provide airflow from the single ventilator to a second patient when the inner housing is in the second airflow position.

6. The airflow switching valve of claim 3, wherein the plurality of positions comprises an intermediate position,
  wherein no first openings of the plurality of first openings through the first wall of the outer housing overlap with any second openings of the plurality of second openings through the surface of the body of the inner housing when the inner housing is in the intermediate position relative to the outer housing.

7. The airflow switching valve of claim 2, wherein the plurality of first openings through the first wall of the outer housing are aligned linearly along the first wall of the outer housing.

8. The airflow switching valve of claim 2, wherein the plurality of second openings through the surface of the body of the inner housing includes two second openings, and wherein one of the two second openings is opposite the other of the two second openings.

9. The airflow switching valve of claim 2, wherein the first wall of the outer housing is a first annular wall, and the track is in or on an inner surface of the first annular wall,
  wherein the body of the inner housing comprises a second annular wall, and
  wherein the plurality of second openings extend through the second annular wall, and the plurality of extensions extend away from an outer surface of the second annular wall.

10. The airflow switching valve of claim 9, wherein the plurality of extensions are pegs.

11. The airflow switching valve of claim 2, wherein the track is wave shaped, the track comprising:
  a first side; and
  a second side opposite the first side,
  wherein each side of the first side and the second side includes a plurality of alternating crest-shaped portions and trough-shaped portions, wherein the plurality of alternating crest-shaped portions and trough-shaped portions of the first side of the track are substantially aligned with the plurality of alternating crest-shaped portions and trough-shaped portions of the second side of the track.

12. The airflow switching valve of claim 11, wherein a plurality of trough-shaped portions of the first side of the track are offset from the plurality of trough-shaped portions of the second side of the track in a first direction, and
  wherein the plurality of crest-shaped portions of the first side of the track are offset from the plurality of crest-shaped portions of the second side of the track in a second direction opposite the first direction.

13. The airflow switching valve of claim 10, wherein an offset in a first direction and the offset in a second direction are configured to allow the inner housing to rotate in a first rotational direction and prevent the inner housing from rotating in a second rotational direction opposite the first rotational direction.

14. The airflow switching valve of claim 2, wherein the inner housing comprises:
  a first section disposed proximate the closed end of the outer housing, the first section including the plurality of extensions and configured to receive the spring; and
  a second section including the plurality of second openings, wherein a first space inside the first section is physically separate from a second space inside the second section.

15. The airflow switching valve of claim 14, wherein the outer housing, the inner housing, the first section of the inner housing, and the second section of the inner housing are cylindrically shaped.

16. The airflow switching valve of claim 2, wherein the first end of the outer housing, the second end of the outer housing, the plurality of first openings through the first wall, the plurality of second openings through the surface of the body, and the plurality of extensions of the inner housing are circular shaped.

17. A system operable to provide artificial respiration to at least two patients using a single ventilator, the system comprising:
  a mechanical ventilator;
  an airflow switching valve, the airflow switching valve comprising:
    an outer housing comprising a plurality of first apertures; and
    an inner housing disposed inside the outer housing, the inner housing comprising a plurality of second apertures;
  at least two patient interfaces;
  at least two one-way valves; and
  an air circuit connecting the mechanical ventilator, the airflow switching valve, and the at least two one-way valves to the at least two patient interfaces, such that the system is operable to provide a breathable gas to the at least two patients.

18. The system of claim 17, wherein the mechanical ventilator is operable to generate an inspiratory breath containing the breathable gas to the air circuit, and
  wherein the air circuit is operable to transfer the inspiratory breath from the mechanical ventilator to the airflow switching valve, and transfer the inspiratory breath from the airflow switching valve to the at least two patient interfaces in an alternating manner depending on a position of the plurality of positions of the inner housing inside the outer housing of the airflow switching valve, such that only a single patient interface of the at least two patient interfaces receives the inspiratory breath.

19. The system of claim 18, wherein the air circuit is operable to transfer an expiratory breath from a patient interface of the at least two patient interfaces to the at least two one-way valves and transfer the expiratory breath from the at least two one-way valves to the mechanical ventilator.

20. The system of claim 17, wherein the airflow switching valve is operable to provide the breathable gas from the mechanical ventilator to a first patient of the at least two patients when the inner housing is in a first position of the plurality of positions, and the airflow switching valve is operable to provide the breathable gas to a second patient of the at least two patients when the inner housing is in a second position of the plurality of positions.

21. The system of claim 20, wherein one first aperture of the plurality of first apertures of the outer housing is aligned with one second aperture of the plurality of second apertures of the inner housing in the first position; and
  wherein another first aperture of the plurality of first apertures of the outer housing is aligned with another second aperture of the plurality of second apertures of the inner housing in the second position.

22. A method for providing inspiratory breaths to multiple patients sharing a single ventilator on an artificial breathing system, the artificial breathing system comprising an airflow switching valve, the airflow switching valve comprising an outer housing and an inner housing, the outer housing comprising a plurality of first apertures and a track, the inner housing comprising a plurality of second apertures and a plurality of extensions, the plurality of extensions being configured to translate within the track of the outer housing to rotate the inner housing between a plurality of positions, the method comprising:

generating, by the single ventilator, a first inspiratory breath for a first patient of the multiple patients;

receiving, by the airflow switching valve, the first inspiratory breath; and providing, by the airflow switching valve, the first inspiratory breath to the first patient of the multiple patients when the inner housing is in a first position of the plurality of positions.

23. The method of claim 22, further comprising:

generating, by the single ventilator, a second inspiratory breath for a second patient of the multiple patients;

receiving, by the airflow switching valve, the second inspiratory breath; and providing, by the airflow switching valve, the second inspiratory breath to the second patient of the multiple patients when the inner housing is in a second position of the plurality of positions.

24. The method of claim 23, further comprising repeating the generating, receiving, and providing for another inspiratory breath for the first patient after the generating, receiving, and providing the second inspiratory breath.

25. The method of claim 22, wherein the first position is when one first aperture of the plurality of first apertures of the outer housing is aligned with one second aperture of the plurality of second apertures of the inner housing.

26. The method of claim 23, wherein the second position is when another first aperture of the plurality of first apertures of the outer housing is aligned with another second aperture of the plurality of second apertures of the inner housing.

27. The method of claim 23, wherein the airflow switching valve further comprises a spring positioned between the outer housing and the inner housing, the spring being compressed in a breath state and extended in a non-breath state, the breath state being when the airflow switching valve receives the first inspiratory breath or the second inspiratory breath, the non-breath state being when the airflow switching valve is not receiving the first inspiratory breath or the second inspiratory breath, wherein receiving the first inspiratory breath causes the inner housing to compress the spring and simultaneously rotate into the first position by way of the plurality of extensions translating within the track of the outer housing, wherein, after providing the first inspiratory breath to the first patient, the spring is configured to extend and cause the inner housing to rotate into an intermediate position by way of the plurality of extensions translating within the track of the outer housing, the intermediate position being between the first position and the second position, wherein receiving the second inspiratory breath causes the inner housing to compress the spring and simultaneously rotate into the second position by way of the plurality of extensions translating within the track of the outer housing, and wherein, after providing the second inspiratory breath to the second patient, the spring is configured to extend and cause the inner housing to rotate into another intermediate position by way of the plurality of extensions translating within the track of the outer housing, the other intermediate position being between the second position and the first position, wherein receiving the second inspiratory breath causes the inner housing to compress the spring and simultaneously rotate into the second position by way of the plurality of extensions translating within the track of the outer housing, and wherein, after providing the second inspiratory breath to the second patient, the spring is configured to extend and cause the inner housing to rotate into another intermediate position by way of the plurality of extensions translating within the track of the outer housing, the other intermediate position being between the second position and the first position.

* * * * *